(12) United States Patent
Schiller et al.

(10) Patent No.: US 6,719,978 B2
(45) Date of Patent: Apr. 13, 2004

(54) VIRUS-LIKE PARTICLES FOR THE INDUCTION OF AUTOANTIBODIES

(75) Inventors: John T. Schiller, Silver Spring, MD (US); Bryce Chackerian, Chevy Chase, MD (US); Douglas R. Lowy, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/835,124

(22) Filed: Apr. 13, 2001

(65) Prior Publication Data

US 2002/0081295 A1 Jun. 27, 2002

Related U.S. Application Data

(63) Continuation of application No. PCT/US99/24548, filed on Oct. 20, 1999.
(60) Provisional application No. 60/105,132, filed on Oct. 21, 1998.

(51) Int. Cl.$^7$ ..................... A61K 39/00; A61K 39/385; C07K 17/00; C07K 17/02; C07K 17/06

(52) U.S. Cl. .................. 424/199.1; 424/194.1; 424/184.1; 424/144.1; 424/143.1; 424/159.1; 424/204.1; 424/147.1; 424/71.1; 424/133.1; 530/350; 435/472; 435/174; 435/235.1

(58) Field of Search ...................... 530/350; 424/184.1, 424/71, 143, 159.1, 204.1, 133.1, 147.1, 199.1, 194.1, 144.1; 435/472, 174, 235.1

(56) References Cited

U.S. PATENT DOCUMENTS

| | | |
|---|---|---|
| 5,437,951 A | 8/1995 | Lowy et al. |
| 5,618,536 A | 4/1997 | Lowy et al. |
| 5,723,287 A | 3/1998 | Russell et al. |

FOREIGN PATENT DOCUMENTS

| | | |
|---|---|---|
| CH | 684782 | 12/1994 |
| EP | 752886 | 1/1998 |
| WO | WO 9929723 | 6/1999 |
| WO | WO 0032227 | 6/2000 |

OTHER PUBLICATIONS

Aichele, P., et al. (1994) Peptide–induced T–cell tolerance to prevent autoimmune diabetes in a transgenic mouse model. *PNAS USA* 91:444–448.
Albert, L.J., et al. (1999) Molecular Mimicry and Autoimmunity. *N. Engl. J. Med.* 341:2068–2074.
Alkhatib, G., et al. (1996) CC CKR5: A Rantes, MIP–1α, MIP–1β Receptor as a Fusion Cofactor for Macrophage–Tropic HIV–1. *Science* 272:1955–1958.
Alkhatib, G., et al. (1997) CC Chemokine Receptor 5–Mediated Signaling and HIV–1 Co–receptor Activity Share Common Structural Determinants. *J. Biol. Chem.* 272:19771–19776.
Atchinson, R.E., et al. (1996) Multiple Extracellular Elements of CCR5 and HIV–1 Entry: Dissociation from Response to Chemokines. *Science* 274:1924–1926.
Bachman, M.F., et al. (1993) The Influence of Antigen Organization on B Cell Responsiveness. *Science* 262:1448–1451.
Bachman, M.F., et al. (1996) The Influence of virus structure on antibody responses and virus serotype formation. *Immunol. Today* 17:553–558.
Bachman, M.F., et al. (1997) Neutralizing Antiviral B Cell Responses. *Annu. Rev. Immunol.* 15:235–270.
Bachman, M.F., et al. (1997) The Role of Antibody Concentration and Avidity in Antiviral Protection. *Science* 276:2024–2027.
Baker T.S., et al. (1991) Structures of bovine and human papillomaviruses Analysis by cryoelectron microscopy and three–dimensional image reconstruction. *Biophys. J.* 60:1445–1456.
Baselga, J., et al. (1996) Phase II Study of Weekly Intravenous Recombinant Humanized Anti–p185$^{HER2}$ Monoclonal Antibody in Patients with HER2/neu–Overexpressing Metastatic Breast Cancer. *J. Clin. Oncol.* 14:737–744.
Bloom, J.W., et al. (1993) Epitope Mapping and Functional Analysis of Three Murine IgG1 Monoclonal Antibodies to Human Tumor Necrosis Factor–α. *J. Immunol.* 151:2707–2716.
Booy, F.P., et al. (1998) Two Antibodies that Neutralize Papillomavirus by Different Mechanisms Show Distinct Binding Patterns at 13 Å Resolution. *J. Mol. Biol.* 281:95–106.
Boring, L., et al. (1996) Molecular Cloning and Functional Expression of Murine JE (Monocyte Chemoattractant Protein 1) and Murine Macrophage Inflammatory Protein 1α Receptors. *J. Biol. Chem.* 271:7551–7558.
Chackerian, B., et al. (1999) Induction of autoantibodies to mouse CCR5 with recombinant papillomavirus particles. *PNAS USA* 96:2373–2378.

(List continued on next page.)

*Primary Examiner*—James Housel
*Assistant Examiner*—Bao Qun Li
(74) *Attorney, Agent, or Firm*—Knobbe, Martens Olson & Bear LLP

(57) ABSTRACT

The invention described herein relates to compositions and methods for stimulating immune responses in vivo against a tolerogen. Novel biotechnological tools, pharmaceuticals, therapeutics and prophylactics, which concern chimeric or conjugated virus-like particles, and methods of use of the foregoing are provided for the study of B cell tolerance and the treatment or prevention of human diseases, which involve the onset of B cell tolerance, such as chronic viral infection, chronic inflammatory disease, and neoplasia.

8 Claims, 7 Drawing Sheets

OTHER PUBLICATIONS

Chackerian, B., et al. (2001) Conjugation of a self–antigen to papillomavirus–like particles allows for efficient induction of protective autoantibodies. *J. Clin. Invest.* 108:415–423.

Chang, T.W. (2000) The pharmacological basis of anti–IgE therapy. *Nat. Biotechnol.* 18:157–162.

Choe, H., et al. (1996) The β–Chemokine Receptors CCR3 and CCR5 Facilitate Infection by Primary HIV–1 Isolates. *Cell* 85:1135–1148.

Chu, R.S., et al. (1997) CpG Oligodeoxynucleotides Act as Adjuvants that Switch on T Helper 1 (Th1) Immunity. *J. Exp. Med.* 186:1623–1631.

Ciapponi, L., et al. (1997) Induction of interleukin–6 (IL–6) autoantibodies through vaccination with an engineered IL–6 receptor antagonist. *Nat. Biotechnol.* 13:997–1001.

Conry, R. M., et al. (Mar. 1995) Breaking tolerance to carcinoembryonic antigen with a recombinant vaccinia virus vaccine in man. *Proceedings of the American Association for Cancer Research.* 36:492 (Abstract 2930).

Dalum, I., et al. (1996) Breaking of B Cell Tolerance Toward a Highly Conserved Self Protein *J. Immunol.* 157:4796–4804.

Dalum, I., et al. (1997) Induction of Cross–reactive Antibodies Against a Self Protein by Immunization with a Modified Self Protein Containing a Foreign T Helper Epitope. *Mol. Immunol.* 34:1113–1120.

Dalum, I., et al. (1999) Therapeutic antibodies elicited by immunization against TNF–α *Nat. Biotechnol.* 17:666–669.

Deng, H., et al. (1996) Identification of a major co–receptor for primary isolates of HIV–1. *Nature* 381:661–666.

Doranz, B.J., et al. (1996) A Dual–Tropic Primary HIV–1 Isolate That Uses Fusin and the β–Chemokine Receptors CKR–5, CKR–3, and CKR–2b as Fusion Cofactors. *Cell* 85:1149–1158.

Dragic, T., et al. (1996) HIV–1 entry into CD4$^+$ cells is mediated by the chemokine receptor CC–CKR–5. *Nature* 381:667–673.

Eck, M.J., et al. (1989) The Structure of Tumor Necrosis Factor–α at 2.6 Å Resolution. *J. Biol. Chem.* 264:17595–17605.

Eigler, A., et al. (1997) Taming TNF: strategies to restrain this proinflammatory cytokine. *Immunol. Today* 18:487–492.

Fehr, T., et al. (1997) Role of Repetitive Antigen Patterns for Induction of Antibodies Against Antibodies. *J. Exp. Med.* 185:1785–1792.

Fitchen, J., et al. (1995) Plant virus expressing hybrid coat protein with added murine epitope elicits autoantibody response. *Vaccine* 13:1051–1057.

Green, N.M. (1965) A Spectrophotmetric Assay for Avidin and Biotin Based on Binding of Dyes by Avidin. *Biochem. J.* 94:23c–24c.

Greenstone, H.L., et al. (1998) Chimeric papillomavirus virus–like particles elicit antitumor immunity against the E7 oncoprotein in an HPV16 tumor model. *PNAS USA* 95:1800–1805.

Han, S., et al. (1997) V(D)J Recombinase Activity in a Subset of Germinal Center B Lymphocytes. *Science* 278:301–305.

Harro, C.D., et al. (2001) Safety and Immunogenicity Trial in Adult Volunteers of a Human Papillomavirus 16 L1 Virus–Like Particle Vaccine. *J. Natl. Cancer Inst.* 93:284–292.

Hedman, K., et al. (1988) Recent Rubella Virus Infection Indicated by a Low Avidity of Specific IgG. *J. Clin. Immunol.* 8:214–221.

Herkel, J., et al. (1997) Humoral Mechanisms in T cell vaccination: Induction and Functional Characterization of Anti–lymphocytic Autoantibodies. *J. Autoimmunity* 10:137–148.

Hertz, M., et al. (1998) Receptor editing and commitment in B lymphocytes. *Curr. Opin. Immunol.* 10:208–213.

Hertz, M., et al. (1998) V(D)J recombinase induction in splenic B lymphocytes is inhibited by antigen–receptor signalling. *Nature* 394:292–295.

Ho, S.N., et al. (1989) Site–directed mutagenesis by overlap extension using the polymerase chain reaction. *Gene* 77, 51–59.

Karlsen, A. E. and Dyrberg, T. (1998) Molecular mimicry between non–self, modified self and self in autoimmunity. *Semin. Immunol.* 10:25–34.

Kim, S.K., et al. (2001) Effect of immunological adjuvant combinations on the antibody and T–cell response to vaccination with MUC1–KLH and GD3–KLH conjugates. *Vaccine* 19, 530–537.

Kimpton, J., et al. (1992) Detection of Replication–Competent and Pseudotyped Human Immunodeficiency Virus with a Sensitive Cell Line on the Basis of Activation of an Integrated β–Galactosidase Gene. *J. Virol.* 66:2232–2239.

Kimbauer, R., et al. (1992) Papillomavirus L1 major capsid protein self–assembles into virus–like particles that are highly immunogenic. *PNAS USA* 89:12180–12184.

Kimbauer, R., et al. (1994) A Virus–Like Particle Enzyme–Linked Immunosorbent Assay Detects Serum Antibodies in a Majority of Women Infected With Human Papillomavirus Type 16, *J. Natl. Cancer Inst.* 86:494–499.

Klareskog, L., et al. (1999) Rheumatoid arthritis and its animal models: the role of TNF–α and the possible absence of specific immune reactions. *Curr. Opin. Immunol.* 11:657–662.

Kuhmann, S.E., et al. (1997) Polymorphisms in the CCR5 Genes of African Green Monkeys and Mice Implicate Specific Amino Acids in Infections by Simian and Human Immunodeficiency Viruses. *J. Virol.* 71:8642–8656.

Lenz, P., et al. (2001) Papillomavirus–Like Particles Induce Acute Activation of Dendritic Cells. *J. Immunol.* 166:5346–5355.

Cole D.J. Inc. (1996) Clinical Protocol Phase I Study of Recombinant CEA Vaccinia Virus Vaccine with Post Vaccination CEA Peptide Challenge. *Human Gene Therapy* 7:1381–1394.

Liu, R., et al. (1996) Homozygous Defect in HIV–1 Coreceptor Accounts for Resistance of Some Multiply–Exposed Individuals to HIV–1 Infection. *Cell* 86:367–377.

Ludmerer, S.W., et al. (1996) Two Amino Acid Residues Confer Type Specificity to a Neutralizing, Conformationally Dependent Epitope on Human Papillomavirus Type 11. *J. Virol.* 70:4791–4974.

Ludmerer, S.W., et al. (1997) A Neutralizing Epitope of Human Papillomavirus Type 11 Is Principally Described by a Continuous Set of Residues Which Overlap a Distinct Linear, Surface–Exposed Epitope, *J. Virol.* 71:3834–3839.

Maini, R.N., et al. (1995) Monoclonal anti–TNFα Antibody as a Probe of Pathogenesis and Therapy of Rheumatoid Disease. *Immunol. Rev.* 144:195–223.

Maini, R.N., et al. (2000) Anti–Cytokine Therpay for Rheumatoid Arthritis. *Annu. Rev. Med.* 51:207–229.

Meyer, A., et al. (1996) Cloning and Characterization of a Novel Murine Macrophage Inflammatory Protein–1α Receptor. *J. Biol. Chem,* 271:14445–14451.

Mijatovic, T., et al. (1997) Interleukin–4 and –13 Inhibit Tumor Necrosis Factor–α mRNA Translational Activation in Lipopolysaccaride–induced Mouse Macrophages. *J. Biol. Chem.* 272:1439–14398.

Müller, et al. (1997) Chimeric Papillomavirus–like Particles. *Virology* 234:93–111.

Nibbs, R.J., et al. (1997) Cloning and Characterization of a Novel Murine β Chemokine Receptor, D6. *J. Biol. Chem.* 272:12495–12504.

Nieland, J.D., et al. (1999) Chimeric papillomavirus virus–like particles induce a murine self–antigen–specific protective and therapeutic antitumor immune response, *J. Cell. Biochem.* 73:145–152. Database Access 1999241917.

Ohashi, P. S., et al. (1991) Ablation of "Tolerance" and Induction of Diabetes by Virus Infection in Viral Antigen Transgenic Mice. *Cell* 65:305–317.

Papavasiliou, F., et al. (1997) V(D)J Recombination in Mautre B Cells: A Mechanism for Altering Antibody Responses. *Science* 278:298–301.

Pegram, M. and Slamon. D. (2000) Biological rationale for HER2/neu (c–erbB2) as a Target for Monoclonal Antibody Therapy. *Semin. Oncol.* 37:13–19.

Picard, L., et al. (1997) Multiple Extracellular Domains of CCR–5 Contribute to Human Immunodeficiency Virus Type 1 Entry and Fusion. *J. Virol.* 71:5003–5011.

Ragupathi, G., et al. (2000) Induction of Antibodies Against GD3 Ganglioside in Melanoma Patients by Vaccination With GD3–Lactone–KHL Conjugate Plus Immunological Adjuvant QS–21. *Int. J. Cancer.* 85:659–666.

Richard, M., et al. (2000) Anti–IL–9 vaccination prevents worm expulsion and blood eosinophilia in *Trichuris muris-*–infected mice. PNAS USA 97:767–772.

Roden, R.B., et al. (1997) Characterization of a Human Papillomavirus Type 16 Variant–Dependent Neutralizing Epitope. *J. Virol.* 71:6247–6252.

Roden, R.B., et al. Neutralization of Bovine Papillomavirus by Antibodies to L1 and L2 Capsid Proteins. (1994) *J. Virol.* 68:7570–7574.

Rose, N.R. (1998) The role of infection in the pathogenesis of autoimmune disease. *Semin. Immunol.* 10:5–13.

Ross, T.M., et al. (1998) Multiple Residues Contribute to the Inability of Murine CCR–5 To Function as a Coreceptor for Macrophage–Tropic Human Immunodeficiency Virus Type 1 Isolates. *J. Virol.* 72:1918–1924.

Rucker, J., et al. (1996) Regions in β–Chemokine Receptors CCR5 and CCR2b That Determine HIV–1 Cofactor Specificity. *Cell* 87:437–446.

Salunke, D.M., et al. (1989) Polymorphism in the assembly of polyomavirus capsid protein VP. *Biophys. J.* 56:887–900.

Samson, M., et al. (1996) Resistance to HIV–1 infection in caucasion individuals bearing mutant alleles of the CCR–5 chemokine receptor gene. *Nature* 382:722–725.

Sano, T. and Cantor, C.R. (1990) Expression of a cloned streptavidin gene *Escherichia coli PNAS USA* 87:142–146.

Sano, T. and Cantor, C.R. (1991) Expression Vectors for Streptavidin–containing Chimeric Proteins. *Biochem. Biophys. Res. Commun.* 176:571–577.

Schenk, D., et al. (1999) Immunization with amyloid–β attenuates Alzheimer–disease–like pathology in the PDAPP mouse. *Nature* 400:173–177.

Steinhoff, U., et al. (1994) Virus or a hapten–carrier complex can activate autoreactive B cells by providing linked T help. *Exp. J. Immunol.* 24:773–776.

Takashima, H., et al. (1992) Characterization of T–cell tolerance to hepatitis B virus (HBV) antigen in transgenic mice. *Immunology* 75:398–405.

Talwar, et al. (1976) Isoimmunization against human chorionic gonadotropin with conjugates of processed β–subunit of the hormone and tetanus toxoid. *PNAN USA* 73:218–222.

Talwar, G.P., et al. (1994) A vaccine that prevents pregancy in women. *PNAS USA* 91:8532–98536.

Trus, B.L., et al. (1997) Novel structural features of bovine papillomavirus capsid revealed by a three–dimensional reconstruction to 9 Å resolution. *Nat. Struct. Biol.* 4:413–420.

Velders, M. P., et al. (1998) Identification of Peptides for Immunotherapy of Cancer. It is Still Worth the Effort. *Crit. Rev. Immunol.* 18:7–27.

Wildbaum, G et al. (2000) A Targeted DNA Vaccine Augments the Natural Immune Response to Self TNF–α and Suppresses Ongoing Adjuvant Arthritis. *J. Immunol.* 163:5860–5866.

William, R.O., et al. (1992) Anti–tumor necrosis factor ameliorates joint disease in murine collagen–induced arthritis. *PNAS USA* 89:9784–9788.

Winkler, C., et al. (1998) Genetic Restriction of AIDS Pathogenesis by an SDF–1 Chemokine Gene Variant. *Science* 279:389–393.

Wirth, S., et al. (1995) Breaking Tolerance Leads to Autoantibody Production but Not Autoimmune Liver Disease in Hepatitis B Virus Envelope Transgenic Mice *J. Immunol.* 154:2504–2515.

Wu, L., et al. (1997) Interaction of Chemokine Receptor CCR5 with its Ligands: Multiple Domains for HIV–1 gp120 Binding and a Single Domain for Chemokine Binding. *J. Exp. Med.* 186:1373–1381.

Wykes, M., et al. (1998) Dendritic Cells Interact Directlfy with Naive B Lymphocytes to Transfer Antigen and Initiate Class Switching in a Primary T–Dependent Response. *J. Immunol.* 161:1313–1319.

Youssef, S. et al. (2000) C–C chemokine–encoding DNA vaccines enhance breakdown of tolerance to their gene products and treat ongoing adjuvant arthritis. *J. Clin. Invest.* 106:361–371.

Zhang L., et al. (1998) In Vivo Distribution of the Human Immunodeficiency Virus/Simian Immunodeficiency Virus Coreceptors: CXCR4, CCR3, and CCR5. *J. Virol.* 72:5035–5045.

Zhang, L.F., et al. (2000) HPV6b virus like particles are potent immunogens without adjuvant in man. *Vaccine* 18:1051–1058.

Zinkemagel, R. M., et al. (1991) T and B cell Tolerance and Responses to Viral Antigens in Transgenic Mice: Implications for the Pathogenesis of Autoimmune versus Immunopathological Disease. *Immunological Reviews.* 122:133–171.

STAINED WITH:

L1-CCR5
IgG

WILD TYPE
L1 VLP
IgG

ANTI-hCCR5
mAb

ANTI-KLHCCR5
IgG

SEQUENCE LISTING

<160> NUMBER OF SEQ ID NOS: 2

<210> SEQ ID NO 1
<211> LENGTH: 16
<212> TYPE: PRT
<213> ORGANISM: Mus musculus

<400> SEQUENCE: 1

His Tyr Ala Ala Asn Glu Trp Val Phe Gly Asn Ile Met Cys Lys Val
1               5                   10                  15

<210> SEQ ID NO 2
<211> LENGTH: 20
<212> TYPE: PRT
<213> ORGANISM: Mus musculus

<400> SEQUENCE: 2

Ser Ser Gln Asn Ser Ser Asp Lys Pro Val Ala His Val Val Ala Asn
1               5                   10                  15

His Gln Val Glu
            20

VIRUS-LIKE PARTICLES FOR THE INDUCTION OF AUTOANTIBODIES

CROSS-REFERENCE TO RELATED APPLICATIONS

This application is a continuation of prior application International Application No. PCT/US99/24548 having international filing date of Oct. 20, 1999, designating the United States of America and published in English, which claims priority of U.S. application Ser. No. 60/105,132, filed Oct. 21, 1998.

FIELD OF THE INVENTION

The present invention relates to compositions and methods for stimulating a B cell immune response in vivo. Novel biological tools, therapeutics, and prophylactics comprising chimeric or conjugated virus-like particles and methods of use of the foregoing are provided for the study, treatment, and prevention of human disease.

BACKGROUND OF THE INVENTION

It is well established that host immune defenses come into play at various stages of human disease. During viral infection, for example, antibodies stimulated in response to previous immunization may neutralize incoming viruses prior to attachment and penetration of susceptible target cells. In the event that cells become infected and display virus-associated antigens on their surfaces, cellular immune responses may also be activated. In this latter case, cytotoxic T cells can kill infected cells, thereby limiting progression of the infection. These humoral and cellular immune responses are commonly mounted against infection by a wide variety of viruses, including viruses having DNA or RNA genomes and outer coats composed of protein capsids or membrane envelopes.

The fact that animals can mount vigorous immune responses to most foreign antigens without similarly responding to components of their own tissues suggested to Burnet and Fenner (*The Production of Antibodies,* Macmillan Co., Melbourne (1949)) that the immune system must have evolved some mechanism for distinguishing self from non-self. A state of self-tolerance undoubtedly exists for central antigens to which the immune system is normally exposed. (See Siskind, G., *Fundamental Immunology* ed. W. E. Paul, Raven Press, New York, Ch. 20 (1984)). A "central antigen" is a self antigen that ordinarily is exposed to cells of the immune system, whereas a "peripheral antigen" is a self antigen that ordinarily is shielded from contact with cells of the immune system, for example by physical separation. Failure of the immune system to mount responses against certain components of the eye, brain and testes, for example, results from segregation of these tissues from the host immune system rather than from self-tolerance. Indeed, autoimmune responses can occur when the physical "barriers" that maintain these peripheral tissue antigens separate from immune surveillance are compromised. Remarkably, the vertebrate genome possesses all of the information needed to produce antibodies directed against a self antigen; and spontaneously generated antibodies to many self antigens can routinely be detected. However, these antibodies are low titer, low avidity and of the IgM class.

Several investigators believe that self-tolerance involves the immune system "learning" to distinguish self and non-self components, an event that occurs before maturing at around the time of birth. It has been speculated that exposure of the lymphoid system to self antigens during fetal development, for example, is a critical phase for developing tolerance to self antigens. According to other models, lymphocytes expressing cell surface receptors specific for the self antigen are eliminated, rendered incapable of activation, or are "tolerized" to the antigen.

The term "B cell tolerance" is often used to describe a state in which the immune system ineffectively responds to the presence of an antigen (e.g., a self antigen) or, more particularly, when the B cells of the immune system fail to mount a response to an antigen. Accordingly, an antigen that is normally exposed to B cells yet fails to induce a high titer antibody response or that is associated with a normal non-response by B cells (e.g., a self antigen) is referred to as a "tolerogen" because the immune system "tolerates" its presence. Clearly, self antigens are tolerogens but foreign antigens can also become tolerogens when B cells fail to sufficiently respond to the antigen. Some investigators believe, for example, that chronic viral infections occur (e.g., viral persistence in infants born to Hepatitis B virus (HBV) carrier mothers) because the immune system has become tolerized to viral antigens. (Takashima et al., *Immunology,* 75:398 (1992)). Tolerogens are not necessarily entire molecules but can be portions of molecules (e.g., peptide fragments of proteins), in potentially immunodominant regions of a molecule. Although investigators have had success in inducing tolerance in animals by various techniques, our understanding of ways to generate antibodies to tolerogens is in its infancy.

SUMMARY OF THE INVENTION

The inventors have discovered compositions and methods of increasing the titers of antibodies to tolerogens (e.g., self antigens and foreign antigens) over those titers routinely generated spontaneously or after conventional methods of vaccination. In several embodiments, the break in B cell tolerance is accomplished by using a support or capsomeric structure having an ordered assembly of subunits or capsid proteins joined to at least one B cell epitope of a tolerogen, wherein the tolerogen is presented in a regular, repetitive array. In some aspects of the invention, the tolerogen and the viral capsid protein are derived from different organisms, viruses, or infectious agents. The support can be a bead, a lipid membrane, or a protein polymer. The capsomeric structure can have icosohedral or helical symmetry. In desirable compositions, however, the capsomeric structure is comprised of viral capsid proteins that self-assemble to form an organized structure referred to as "virus-like particle," or VLPs.

In some embodiments, the viral capsid proteins are hybrid molecules or are otherwise modified. Thus, some embodiments are "chimeric virus-like particles (VLPs)" and others are "conjugated virus-like particles (VLPs)", wherein "chimeric VLPs" have a tolerogen joined to the viral capsid protein (or its homolog) by genetic engineering (e.g., creation of a tolerogen/capsid protein fusion) and "conjugated VLPs" have a tolerogen joined to the viral capsid protein (or its homolog) by way of chemical, physical or other modification of the capsid protein or tolerogen or both (e.g., biotin/streptavidin, biotin/avidin, other ligand/receptor sequences). Thus, aspects of the invention include a composition comprising a support having an ordered assembly of subunits and at least one B cell epitope of a tolerogen joined to the support so as to form a tolerogen-presenting immunogen, wherein the tolerogen-presenting immunogen displays the tolerogen in a regular, repetitive array. Other compositions of the invention comprise a capsomeric structure having a symmetrical assembly of capsid proteins and at least one B cell epitope of a tolerogen joined to the capsomeric structure so as to form a tolerogen presenting virus-like particle (VLP), wherein the tolerogen presenting VLP displays the tolerogen in an ordered, repetitive array. Another embodiment of the invention concerns an isolated complex comprising one of these compositions joined to a cell of the immune system. Further, pharmaceuticals comprising these compositions are embodiments of the invention.

Methods of generating antibodies to a tolerogen are also part of the invention. By one method, antibodies to a tolerogen are generated by identifying a subject in need of antibodies to a tolerogen and providing to the subject a sufficient amount of one of the compositions described above so as to generate antibodies to the tolerogen. Another approach involves the identification of agents that generate auto-antibodies. Accordingly, one of the compositions above is provided to a subject, antibodies are isolated from the subject, the titer of the antibodies isolated in step (b) that bind to the tolerogen are determined and the agent is identified by the ability to generate high titer antibodies. Additionally, a method of generating monoclonal antibodies to a tolerogen is within the scope of the invention. By this approach, one of the compositions described above is provided to a subject and a hybridoma is made with a B cell from the subject. Other methods include a method of enhancing the production of antibodies to a normally immunogenic compound comprising the steps of selecting an antigen that generates a low titer antibody response in a subject, joining this antigen to a modified VLP so as to form a conjugated VLP, wherein the conjugated VLP displays the antigen in a regular repetitive array, and providing the conjugated VLP to a subject and thereby generating high titer antibodies.

BRIEF DESCRIPTION OF THE DRAWINGS

FIG. 1A shows IgG antibody reactivity to BSA-coupled CCR5 peptide. FIG. 1B shows IgG antibody reactivity to BPV-1 VLPs. Symbols represent results using sera from mice inoculated with L1-CCR5 particles (■), denatured L1-CCR5 particles (♦), or BPV-1 VLPs (Δ) in the presence of Freunds adjuvant, or L1-CCR5 particles in the absence of adjuvant (○).

DETAILED DESCRIPTION OF THE INVENTION

Figure 1A:
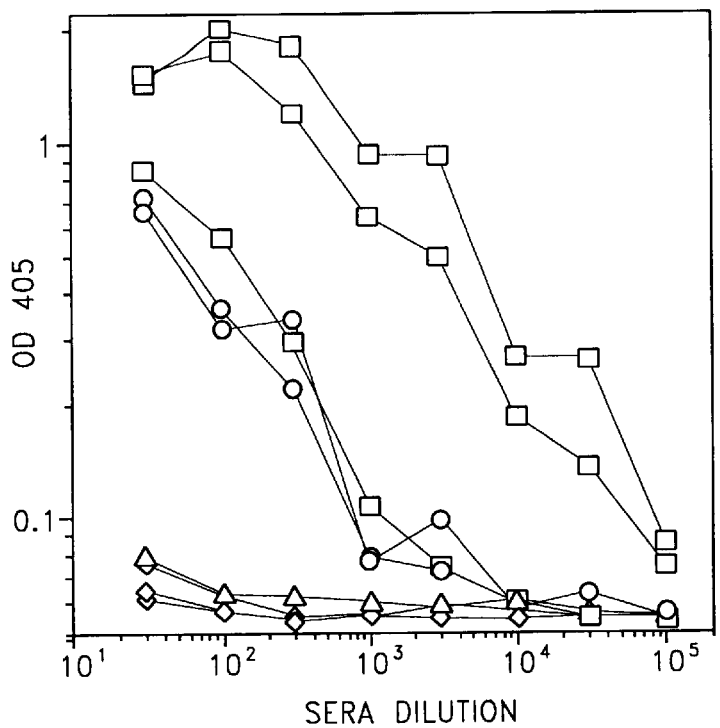
FIGS. 1A and 1B are line graphs showing serum antibody reactivity in an ELISA assay.

The invention described herein concerns compositions and methods of increasing the titers of antibodies to "tolerogens," including self antigens and foreign antigens, over those titers routinely generated spontaneously or after conventional methods of vaccination. By "low titer antibody response" is meant a B cell response that results in an insufficient amount of antibodies to mount a physiologically effective in vivo immune response, whereas, a "high titer antibody response" refers to a sufficient amount of antibodies to mount a physiologically effective immune response in vivo. The terms "low titer antibody response" and "high titer antibody response" are also defined according to the concentration and avidity of the antibody produced. That is, whether an antigen produces a "low titer antibody response" or a "high titer antibody response" depends on the dilution of antibody containing sera at which antigen is no longer detectable in an ELISA assay, wherein 200 ng of target antigen is typically used with a 1:1000 dilution of secondary antibody. Thus, a "low titer antibody response" is typically less than about a 1:10000 dilution under the conditions for ELISA described above and a "high titer antibody response" is typically greater than or equal to a 1:10000 dilution. It should be understood that the term "tolerogen" is used throughout this disclosure to refer to a self antigen or foreign antigen (peptide, nucleic acid, carbohydrate, or lipid) that is either associated with complete B cell non-responsiveness or limited B cell responsiveness in that the antigen elicits only a low titer antibody response that does not substantially affect the normal in vivo activity of the antigen.

In several embodiments, the break in B cell tolerance is accomplished by using a support or capsomeric structure having an ordered assembly of subunits or capsid proteins joined to at least one B cell epitope of a tolerogen, wherein the tolerogen is presented in a regular, repetitive array. In some aspects of the invention, the tolerogen and the viral capsid protein are derived from different organisms, viruses, or infectious agents. The support can be a bead, a lipid membrane, or a protein polymer. The capsomeric structure can have icosohedral or helical symmetry. In desirable compositions, however, the capsomeric structure is comprised of viral capsid proteins that self-assemble to form an organized structure. Such viral capsid assemblies are referred to as "virus-like particle," or VLPs.

In some embodiments, the viral capsid proteins are hybrid molecules or are otherwise modified. The term "virus-like particle" or "capsomeric structure" is often used to refer to an organized structure comprising self-assembling ordered arrays of capsid proteins that do not include a viral genome. In this respect, some embodiments are "chimeric virus-like particles (VLPs)" and others are "conjugated virus-like particles (VLPs)". The term "chimeric VLP" refers to a VLP where the tolerogen is joined to the viral capsid protein (or its homolog) by genetic engineering (e.g., creation of a tolerogen/capsid protein fusion). Thus, the tolerogen/capsid protein fusion is often referred to as a "hybrid coat protein" because the viral coat protein is chimerized with an amino acid sequence from the B cell epitope of a tolerogen. According to the nomenclature used herein, a hybrid coat protein is identified by the name of the viral coat protein and the source of the tolerogen that is displayed in connection with the viral coat protein. The term "conjugated VLP" is used to refer to a VLP where the tolerogen is joined to the viral capsid protein (or its homolog) by way of chemical, physical or other modification of the capsid protein or tolerogen or both (e.g., biotin/streptavidin, biotin/avidin, other ligand/receptor sequences).

The hybrid coat protein can incorporate the amino acid sequence of the tolerogen within its primary structure, as by inserting the amino acid sequence of the tolerogen into the amino acid sequence of the viral coat protein, or by replacing the amino acid sequence of the viral coat protein with the amino acid sequence of the tolerogen. The site of chimerization oftentimes depends on the outer surface of the VLP and regions of the viral coat protein that are involved in self-assembly. This site can correspond to the site of a virus neutralizing epitope, for example. It is to be understood that the hybrid coat protein can take the form of a single coat protein in certain embodiments of the invention, a capsomere (5 coat proteins arranged in a pentamer) in other embodiments, or a VLP composed of multiple capsid proteins arranged as a particulate structure in preferred embodiments.

The viral capsid protein that comprises the capsomeric structure of a VLP can be from many different types of viruses but desirable embodiments have proteins that are found in a virus having an icosohedral structure (e.g., T=7) and viruses whose natural reservoir host is mammal and viruses selected from the families papillomavirinae, polyomavirinae, or parvoviridae. Preferred compositions have a capsid assembly comprising a plurality of papillomavirus hybrid or modified L1 proteins.

By employing the chimeric and conjugated VLP technology disclosed herein, several approaches can be used to join a tolerogen to a support so as to create many novel compositions. In most embodiments, the composition is a "multimeric" support in that more than one tolerogen molecule is attached to the support. In some embodiments, however, a "multimerized" support is provided in that the tolerogen portion of the composition comprises a plurality of the same tolerogen domain fused in tandem. Further, multimeric compositions having multimerized tolerogens are also embodiments of the invention. In other embodiments, the composition is a "composite" support in that more than one type of tolerogen is presented. One of skill in the art will also appreciate that composite supports can be multimeric and can include multimerized tolerogens. Preferably, the multimeric compositions, multimerized compositions, and composite compositions and combinations thereof join tolerogens to the support in a manner that optimizes presentation to cells of the immune system. For example, the embodiments present the tolerogens in an ordered, closely spaced, repetitive array. Additionally, some embodiments include linkers engineered between the support and the viral capsid protein (or its homolog) or between the tolerogen and the viral capsid protein (or its homolog) or both so as to reduce steric hindrance and encourage optimal immune response. Thus, some compositions have a viral capsid protein (or its homolog) or a tolerogen or both that are joined to the support by way of a linker.

Many different tolerogens can be joined to the support including peptides, nucleic acids, carbohydrates, and lipids. In some embodiments, the tolerogen is a self antigen. For example, the tolerogen can be a ligand, such as a protein on the surface of a neoplastic cell, or a growth factor, such as a protein associated with angiogenesis, or a viral receptor, such as the chemokine receptor CCR5, and cytokines, such as TNF-α. Fragments of these "full-length" tolerogens are also desirable for some embodiments. That is, in some embodiments the tolerogen can be an entire molecule (e.g., full-length) but most often, the tolerogen comprises only a portion or fragment of the full-length molecule (e.g., partial-length). Desirable tolerogens comprise at least 5 to 500 consecutive amino acids of the full-length molecule, advantageously 5 to 200, and preferably 5 to 50. Preferably, the tolerogen and the viral capsid protein are derived from different organisms, viruses, or infectious agents. Other embodiments include an isolated complex comprising one of the compositions described above joined to a cell of the immune system (e.g., a B cell, a T cell, or a dendritic cell) and a pharmaceutical comprising one of the compositions described above.

The compositions, isolated complexes, and pharmaceuticals of the invention are used as biological tools, therapeutics, and prophylactics for the study of B cell tolerance, identification of agents that generate autoantibodies, and treatment and prevention of human diseases, such as viral infection, chronic inflammation, and cancer. In one embodiment, for example, a method to identify agents that generate autoantibodies is provided. By this approach, a composition of the invention is provided to a subject, antibodies are then isolated from the subject, and a determination of whether the isolated antibodies interact with the tolerogen presented by the composition is made. Subsequently, the immunogen is identified as one that breaks B cell tolerance by the ability of the isolated antibodies to interact with the tolerogen. In another embodiment, a method of generating antibodies to a tolerogen is provided in which a subject in need of antibodies to a tolerogen is identified and then is provided a therapeutically beneficial amount of a composition of the invention. Additionally, methods of treatment and prevention of HIV infection, chronic viral infection, cancer and inflammation are provided, which involve the step of providing a pharmaceutical comprising a composition of the invention. For example, breast cancer and rheumatoid arthritis can be treated by inducing the production of antibodies directed against ErbB-2 and TNF-α, respectively. (Maini, R. N. et al., Imm. Reviews, 144:195–223 (1995); Baselga, J. et al., J. Clin. Oncol., 14:737–44 (1996)). Further, polyclonal and monoclonal antibodies directed to epitopes on the chimeric and conjugated VLPs of the invention are embodiments.

Evidence of our discovery is provided in two groups of experiments provided below. In a first exemplary demonstration, B cell tolerance to the mouse chemokine receptor (mCCR5) central antigen was abrogated by immunizing mice with chimeric VLPs having the mCCR5 tolerogen. In these experiments, a peptide representing an extracellular loop of the mouse chemokine receptor CCR5 was incorporated into a neutralizing epitope of the bovine papillomavirus virus L1 coat protein (BPV-1) by conventional cloning techniques. L1 has the intrinsic capacity to self-assemble into virus-like particles (VLPs) that induce high levels of neutralizing antibodies, even without adjuvant. (Kimbauer, R. et al., Proc. Natl. Acad. Sci., USA, 89:12180–12184 (1992); Greenstone, H. L. et al., Proc. Natl. Acad. Sci. USA, 95:1800–1805 (1998)). The CCR5 receptor is expressed in numerous cell types and tissues, including memory T cells and macrophages. (Zhang, L. et al., J. Virol., 72:5035–5045 (1998)) Recombinantly produced chimeric proteins called "L1-CCR5S" self-assembled into particulate structures having an ordered array of capsomeres (hereafter designated as virus-like particles or VLPs) that were used as immunogens. Those having ordinary skill in the art will appreciate that CCR5 is known to be the co-receptor for M-tropic strains of HIV, and that monoclonal antibodies to human CCR5 block HIV infection of human cells in vitro.

As detailed below, mice administered with the L1-CCR5 immunogen produced auto-antibodies that bound to native mouse CCR5, inhibited binding of the RANTES ligand, and blocked HIV-1 infection of an indicator cell line that expressed a human-mouse CCR5 chimera. We also show that the long-term effects of the treatment protocol on mice were minimal. Further, we demonstrate that auto-antibodies to CCR5 can be produced in primates. These experiments provide evidence that B cell tolerance to a cell surface self antigen that has co-evolved with an immune system can be broken. These novel compositions can be incorporated into pharmaceuticals and can be used to treat and/or prevent HIV infection.

In a second group of experiments, we provide evidence that the production of autoantibodies to Tumor Necrosis Factor-α (TNF-α) can be induced by inoculating a subject with conjugated VLP comprising a fragment of TNF-α. The immunogen was created by joining a streptavidin/TNF-α fusion protein (SA-TNF-α) to biotinylated L1-VLPs. Mice inoculated with SA-TNF-α VLP conjugates produced auto-antibodies that neutralized the effects of TNF-α on a TNF-α sensitive cell line (L929 cells). These novel compositions can be incorporated into pharmaceuticals and can be used to treat and/or prevent chronic inflammatory disease and other diseases associated with excessive release of TNF-α including, but not limited to, rheumatoid arthritis, Crohn's disease, ulcerative colitis, cancer, disseminated sclerosis, diabetes, psoriasis, osteoporosis, and asthma. In the disclosure below and the examples that follow, we discuss these two groups of experiments in greater detail.

A Chimeric VLP that Breaks Immune Tolerance and Inhibits HIV Infection

While investigating whether auto-antibodies against a self antigen can be induced, we discovered that B cell tolerance can be abrogated by placing the antigen in a context that mimics the ordered surface of a viral particle. In our initial experiments, we inserted the mouse chemokine receptor mCCR5 into an immunodominant site of the bovine papillomavirus L1 coat protein. The recombinant protein was called "L1-CCR5 ", which is a self-assembling chimeric L1 protein that includes a plurality of amino acids encoding a CCR5 epitope. Papillomaviruses were selected because they are highly specific immunogens. Each vertebrate species is infected by a distinct group of papillomaviruses, with each group comprising several papillomavirus types. Neutralizing antibodies against the virions of one papillomavirus type do not ordinarily confer immunity against another type.

Papillomaviruses are examples of non-enveloped viruses that replicate in the epithelia of a wide variety of animal species to result in the formation of benign epithelial and fibro-epithelial tumors or warts. Papillomavirus particles are about 55 nm in diameter and encapsidate an approximately 8 kb double-stranded DNA genome contained in a nucleo-histone core (Baker et al., Biophys J., 60:1445 (1991)). The capsids are composed of two virally encoded proteins, L1 and L2, that migrate on SDS-PAGE gels at approximately 55 kDa and 75 kDa, respectively (Mose Larson et al., J. Virol., 61:3596 (1987)). The L1 major capsid protein is arranged in 72 pentamers which associate with T=7 icosahedral symmetry. There are approximately 12 L2 capsid proteins per virion. (Baker et al., Biophys J., 60:1445 (1991)).

The L1 protein has the capacity to self-assemble so that large amounts of virus-like particles (VLPs) can be generated by expression of the L1 protein from a given papillomavirus in a variety of recombinant expression systems. (Kimbauer et al., Proc. Natl. Acad. Sci. USA, 89:12180 (1992) (BPV-1, baculovirus expression system); Hagensee et al., J. Virol., 67:315 (1993) (HPV-1, vaccinia virus expression system); Kimbauer et al., J. Virol., 67:6929 (1993) (HPV-16, baculovirus expression system); Rose et al., J. Virol, 67:1936 (1993) (HPV-11, baculovirus expression system); Sasagawa et al., Virol., 206:126 (1995) (HPV-16, yeast expression system); Nardinelli-Haefliger et al., Infection and Immunity, 65:3328 (1997) (HPV-16, bacterial expression system)). Although not required for assembly, L2 is incorporated into VLPs when co-expressed with L1 (L1/L2 VLPs) in cells.

Immunization of rabbits with native virions or L1 VLPs, but not with denatured L1 proteins, induces high titers of neutralizing serum antibodies (Christensen et al., J. Virol., 64:3151 (1990); Kirnbauer et al., *Proc. Natl. Acad. Sci USA,* 89:12180 (1992); Pilacinski et al., *Bio/Technology,* 2:356 (1984); Segre et al., *Am. J. Vet. Res.,* 16:517 (1955)). The polyclonal and monoclonal neutralizing antibodies generated against native particles recognize conformationally dependent epitopes (Christensen et al., *Virus Res,* 28:195 (1993); Christensen et al., *Virology,* 181:572 (1991)). Although, the nature of the humoral immune response against papillomavirus antigens is well established, no one appreciated or expected that the ordered geometry of L1 VLPs could be exploited to present a tolerogen to the immune system in a manner that promotes a potent immune response and, thus, breaks B cell tolerance.

Generation of chimeric L1-CCR5 particles required inserting the CCR5 peptide into a region of L1 that would not disrupt the ability of L1 to form particles. (See Example 1). Although the precise structural location and function of most L1 amino acids are not known, amino acid changes that disrupt the neutralizing epitopes of various human papillomaviruses without affecting capsid assembly have been mapped to three non-contiguous regions of L1. (Ludmerer, S. W., Benincasa, D. & Mark III, G. E., *J. Virol.,* 70:4791–4794 (1996); Ludmerer, S. W. et al., *J. Virol.,* 71:3834–3839 (1997); Roden, R. B. et al., *J. Virol.,* 71:6247–6252 (1997)). As it was likely that amino acids at these sites were on the surface of the capsid, the analogous sites in BPV-1 L1 were targeted for peptide insertion. Therefore, three L1-CCR5 chimeras were constructed in which the L1 sequence at BPV-1 L1 amino acids 130–136, 275–285, or 344–350 was replaced with a sequence predicted to encode a 16 amino acid peptide corresponding to the first EC loop of mouse CCR5 (mCCR5) from C57B1/6 (B6) mice. These chimeras were designated L1-CCR5 chimeras 1, 2, and 3, respectively.

Recombinant baculoviruses containing L1-CCR5 chimeras were generated, and the resulting L1-CCR5 particles were purified by gradient centrifugation. (Kirubauer, R. et al., *Proc. Natl. Acad. Sci. USA,* 89:12180–12184 (1992)). To determine if the chimeric L1-CCR5 molecules assembled into VLPs, capsomeres, or other particulate forms, Superose 6 gel filtration chromatography was performed on preparations of the three L1-CCR5 chimera. (See Example 2). Only preparations of L1-CCR5 chimera 1 eluted in a fraction indicating an assembled particulate structure. Therefore, further analysis was limited to this chimera. Examination of chimera 1 particles by electron microscopy revealed many particles which were smaller than wild type L1 VLPs, approximately 28 nm vs 55 nm. Morphologically, the L1-CCR5 chimeric particles resembled polyomavirus 12 ICOSA shells (T=1 particles), which are composed of a regular array of 12 pentameric capsomers of the polyomavirus major coat protein VP1, and can be generated upon in vitro reassembly of VP1 capsomeres at high ionic strength. (Salunke, D., Caspar, D. L. D. & Garcea, R. L., *Biophysical Journal,* 56:887–900 (1989)). Small particles of a similar size to the L1-CCR5 particles are often found as a minor component of wild type BPV-1 L1 VLP preparations.

Figure 1B:
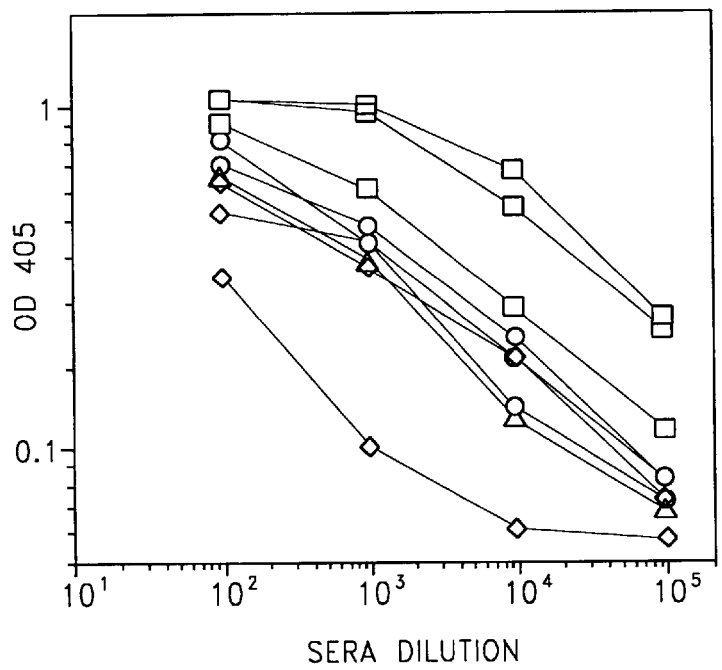

To examine whether the CCR5 chimeric particles could induce anti-CCR5 antibodies, C57B1/6 mice (a strain which encodes the identical CCR5 sequence as the insert sequence) were vaccinated with L1-CCR5 particles, denatured L1-CCR5 protein, or wild type VLPs. (See Example 3). Sera from these mice were tested for reactivity to CCR5 peptide and wild type VLPs by ELISA (FIG. 1A). Sera from control mice inoculated with wild type VLPs had no anti-CCR5 ELISA reactivity, but inoculation with L1-CCR5 particles induced sera with high anti-CCR5 ELISA titers. These titers ranged from $3 \times 10^3$ to $3 \times 10^4$ in the three animals inoculated in combination with Freund's adjuvant, and measured $3 \times 10^3$ in the two animals inoculated without adjuvant. In contrast, no CCR5-peptide-specific antibodies were detected in mice inoculated with denatured L1-CCR5 particles in combination with adjuvant. The lack of reactivity of the denatured L1-CCR5 particles was limited to the CCR5 peptide, since the denatured material elicited high titers of anti-L1 antibodies (FIG. 1B).

Figure 2A:
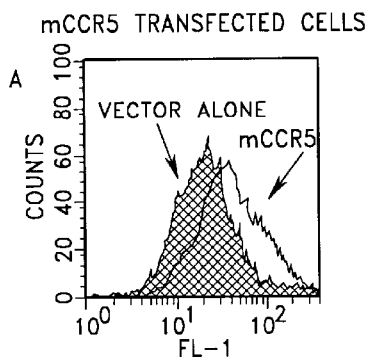
FIGS. 2A–2G are histograms illustrating flow cytometric analysis of antibody binding to transiently transfected HeLa-MAGI cells. Constructs encoding CCR5 DNA (thick solid line) or, as a control for background staining, vector alone (shaded histogram), were transfected into the cells 2 days prior to staining. (2A–2D). Cells transfected with mouse CCR5 or vector DNA. (2E–2G). Cells transfected with a human/mouse CCR5 chimera (HMHH) or vector DNA. Cells were incubated with purified IgG from L1-CCR5 immunized mice (2A and 2E), purified IgG from BPV-1 VLP immunized mice (2B and 2F), or purified IgG from KLH coupled CCR5 peptide immunized mice (2D). As a control, cells were also stained with a flourescein-labelled monoclonal antibody against the 2nd EC loop of human CCR5 (2C and 2F).
Figure 2E:
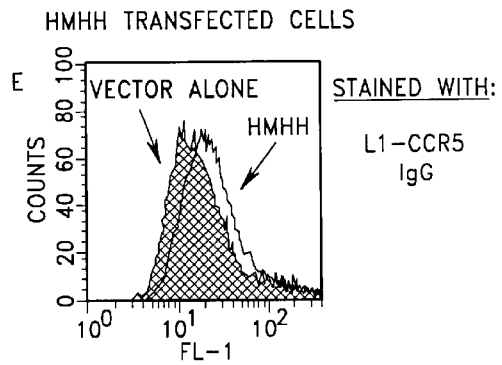
Figure 2B:
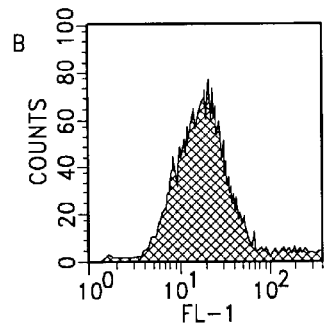
Figure 2F:
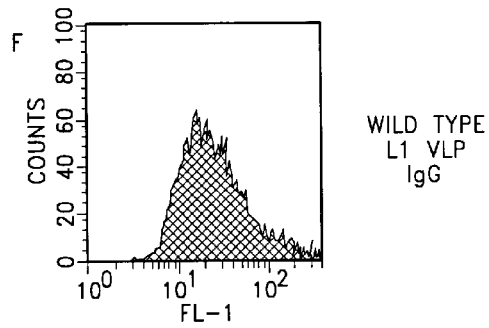
Figure 2C:
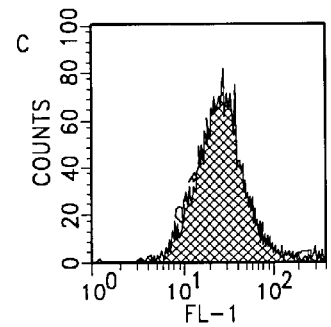
Figure 2G:
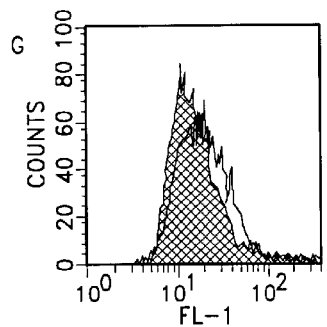
Figure 2D:
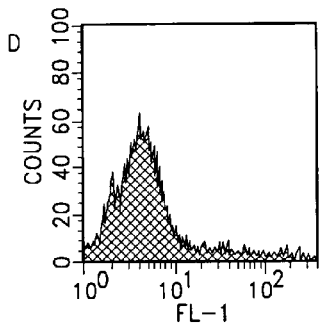

While these results provided evidence that the L1-CCR5 particles elicit antibodies to the CCR5 peptide, the possibility existed that these antibodies might not recognize the peptide in its native conformation as part of membrane associated mCCR5. To eliminate this possibility, an experiment was performed in which the ability of anti-CCR5 antibodies to bind to mCCR5 on cells was tested by flow cytometric (FACS) analysis. (See Example 4). The binding of L1-CCR5 particle sera to mCCR5 expressed on primary mouse T cells and macrophages could not be assessed because of high levels of non-specific mouse IgG binding to these cells. Alternatively, cloned mCCR5 from B6 mice was transiently expressed in HeLa-MAGI cells by transfection, and the binding of purified mouse IgG was measured relative to vector transfected cells (FIGS. 2A–2G). By this assay, IgG from L1-CCR5 immunized mice bound specifically to the mCCR5 transfected cells (FIG. 2A), whereas there was no significant binding with purified IgG from wild type BPV VLP sera (FIG. 2B), or with a monoclonal antibody (mAB182) that binds to the second EC loop of human (h) CCR5 (FIG. 2C). As a control for antibody specificity, mice were inoculated with mCCR5 peptide coupled to keyhole limpet hemocyanin (KLH). While these mice generated an anti-CCR5 peptide antibody response, with ELISA titers of $10^5$ against CCR5 peptide coupled to bovine serum albumin (BSA), the IgG purified from the sera of these mice failed to bind mCCR5 expressing cells (FIG. 2D). Thus, the L1-CCR5 induced antibodies, in contrast to those induced by the KLH-coupled peptide, function as true auto-antibodies, in that they bind native mCCR5.

Figure 3:
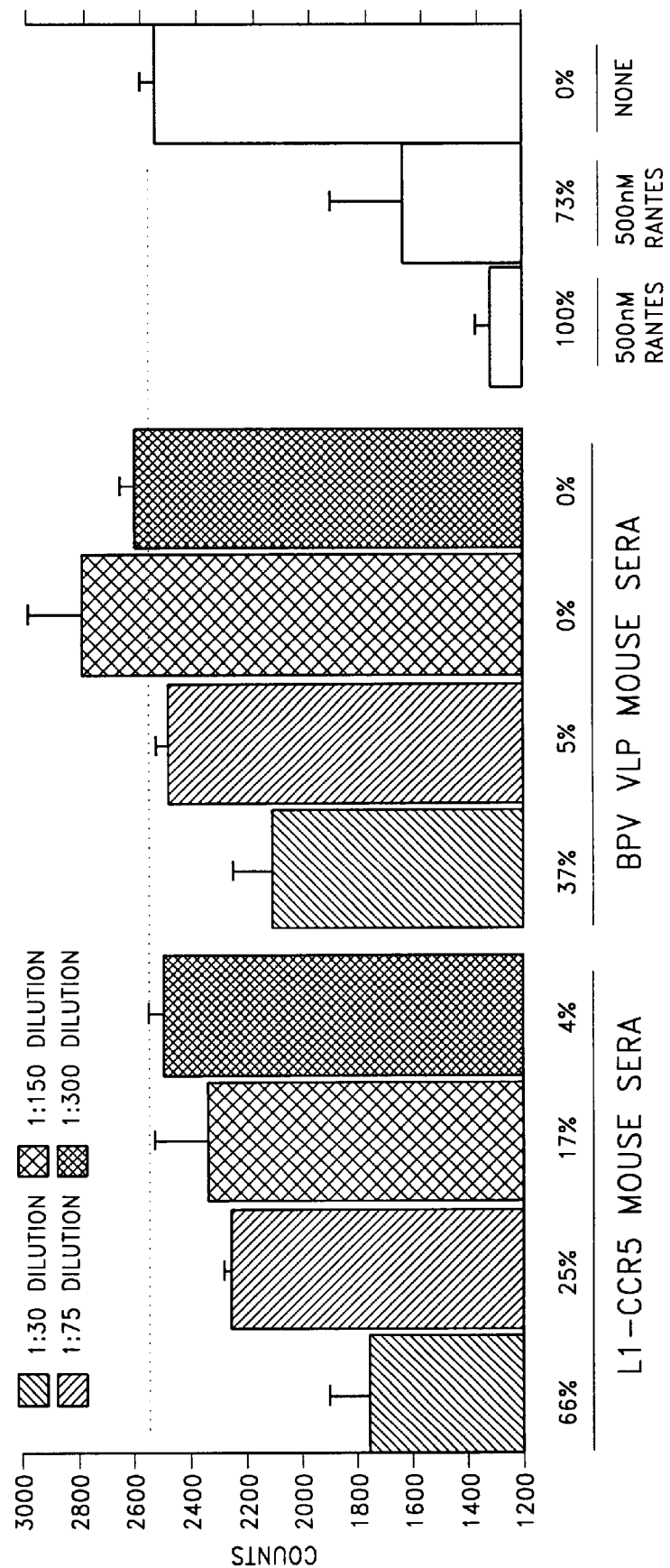
FIG. 3 is a bar graph representing displacement of iodinated human RANTES by sera. HeLa-MAGI cells were transiently transfected with mCCR5. Three days after transfection, cells were incubated with 0.5 nM iodinated RANTES in the absence or presence of dilutions of mouse sera. Maximally bound iodinated RANTES was determined by assaying for binding in the absence of sera, and corresponds to approximately 2550 cpm (indicated by the dashed line). Non-specific binding of iodinated RANTES (approximately 1300 cpm) was determined by assaying for binding in a 1000-fold excess (500 nM) of cold (non-iodinated) human RANTES. Data represents the average of duplicate wells from one experiment. This assay was repeated on two occasions to ensure reproducibility.

As another approach to examine the ability of the antibodies to bind native mCCR5, we examined whether the L1-CCR5 sera could compete with a chemokine ligand for mCCR5 for binding to HeLa-MAGI cells transiently transfected with mCCR5 (FIG. 3). (See Example 5). The mouse chemokines MIP-1α, MIP-1β, and RANTES are ligands for mCCR5. In addition, the human homologs of MIP-1β and RANTES are able to bind to mCCR5. (Meyer, A. et al., *J. Biol. Chem.,* 271:14445–14451 (1996); Nibbs, R. J. B. et al., *J. Biol. Chem.,* 272:12495–12504 (1997)). In the competition assay, commercially available iodinated human RANTES was used. A 1:30 dilution of L1-CCR5 sera displaced approximately 66% of the iodinated human RANTES (similar to the displacement observed using a 100-fold excess of cold RANTES), compared with 37% displacement with a 1:30 dilution of wild type L1 VLP sera. The 1:75 and 1:150 dilutions of L1-CCR5 sera displaced 25% and 17% of the iodinated RANTES, respectively, whereas no significant displacement was observed using control sera at these dilutions. Previous studies have shown that MIP-1α, MIP-1β, and RANTES bind to the to 2nd EC loop of hCCR5, since their binding was blocked by monoclonal antibody to this loop but not by antibody to the amino terminus of hCCR5. (Wu, L. et al, *J. Exp. Med.,* 186:1373–1381 (1997)). Our results from these experiments provides evidence that antibodies binding to the first EC loop of mCCR5, which is located between these two sites, can partially block RANTES binding, perhaps because of the proximity of this loop to the 2nd EC loop.

The ability of L1-CCR5 induced antibodies to block M-tropic HIV-1 infection was also tested. (See Example 6). The interaction between HIV-1 envelope and hCCR5 is complex, likely strain dependent, and probably involves several EC regions of CCR5. Specifically, monoclonal antibody studies have implicated the 2nd EC loop and the $NH_2$-terminal region of hCCR5, and studies of chimeric receptors have indicated that the first and third EC loops of hCCR5 also contribute to its interaction with HIV-1. (Wu, L. et al., *J. Exp. Med.,* 186:1373–1381 (1997); Rucker, J. et al., *Cell,* 87:437–446 (1996); Atchison, R. E. et al., *Science,* 274:1924–1926 (1996); Alkhatib, G. et al., *J. Biol. Chem.,* 272:19771–19776 (1997); Picard, L. et al., *J. Virol.,* 71:5003–5011 (1997); Ross, T. M., Bieniasz, P. D. & Cullen, B. R., *J. Virol.,* 72:1918–1924 (1998)). Although mCCR5 does not function as an HIV-1 coreceptor, a human-mouse chimeric receptor (HMHH), which contains the first EC loop of mCCR5 (the B6 mouse sequence) in a background of hCCR5, has coreceptor activity (albeit at low efficiency) when expressed in human cell lines. (Kuhmann, S. E. et al., *J. Virol,* 71:8642–8656 (1997)). We used this chimeric receptor to test whether L1-CCR5 sera could block M-tropic HIV-1 infection. To confirm that IgG purified from L1-CCR5 sera would bind HMHH, FACS analysis was performed on HeLa-MAGI cells transiently transfected with HMHH. Positive binding was obtained with IgG from L1-CCR5 mice and with a positive control monoclonal antibody that binds to the 2nd EC loop of human CCR5, while IgG from wild type L1 VLP mice did not bind HMHH (FIGS. 2E-2G).

Figure 4:
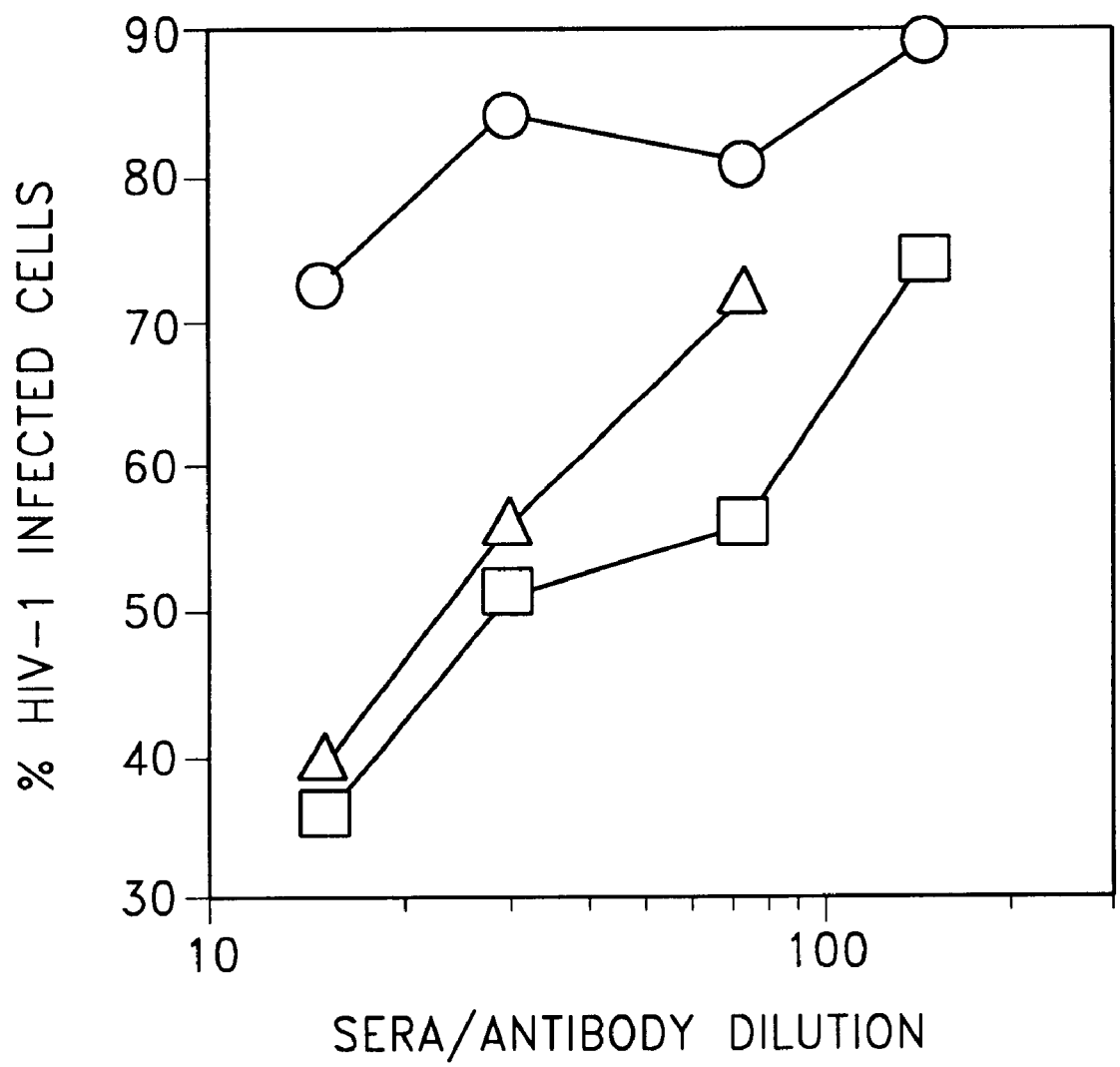
FIG. 4 is a line graph showing inhibition of HIV-1 BaL infection using dilutions of L1-CCR5 sera, BPV-1 VLP sera, or a monoclonal antibody against the second EC loop of human CCR5 (mAB182). Sera was pooled from three animals. HeLa-MAGI cells, an HIV-1 indicator cell line in which the nuclei of infected cells stain blue, were transiently transfected with a human-mouse CCR5 chimera (HMHH), which contains the first EC loop of mouse CCR5 in a background of the human CCR5 gene. Three days after transfection, cells were incubated with dilutions of pooled mouse sera or antibody for 30 minutes at 40° C. Cells were then challenged with the M-tropic isolate HIV-1 BaL. Three days after infection, infected cells were scored by counting the number of blue cells in each well. Inhibition of HIV-1 BaL infection was determined by comparing the number of blue (infected) nuclei in the presence of sera versus the number of blue nuclei in the absence of sera. Data represents the average of duplicate wells from one experiment. To ensure reproducibility, this assay was repeated on at least two other occasions, with similar results. Sera from (■) L1-CCR5 inoculated mice, (○) BPV-1 VLP inoculated mice, or (Δ) mAB182.
Figure 5:
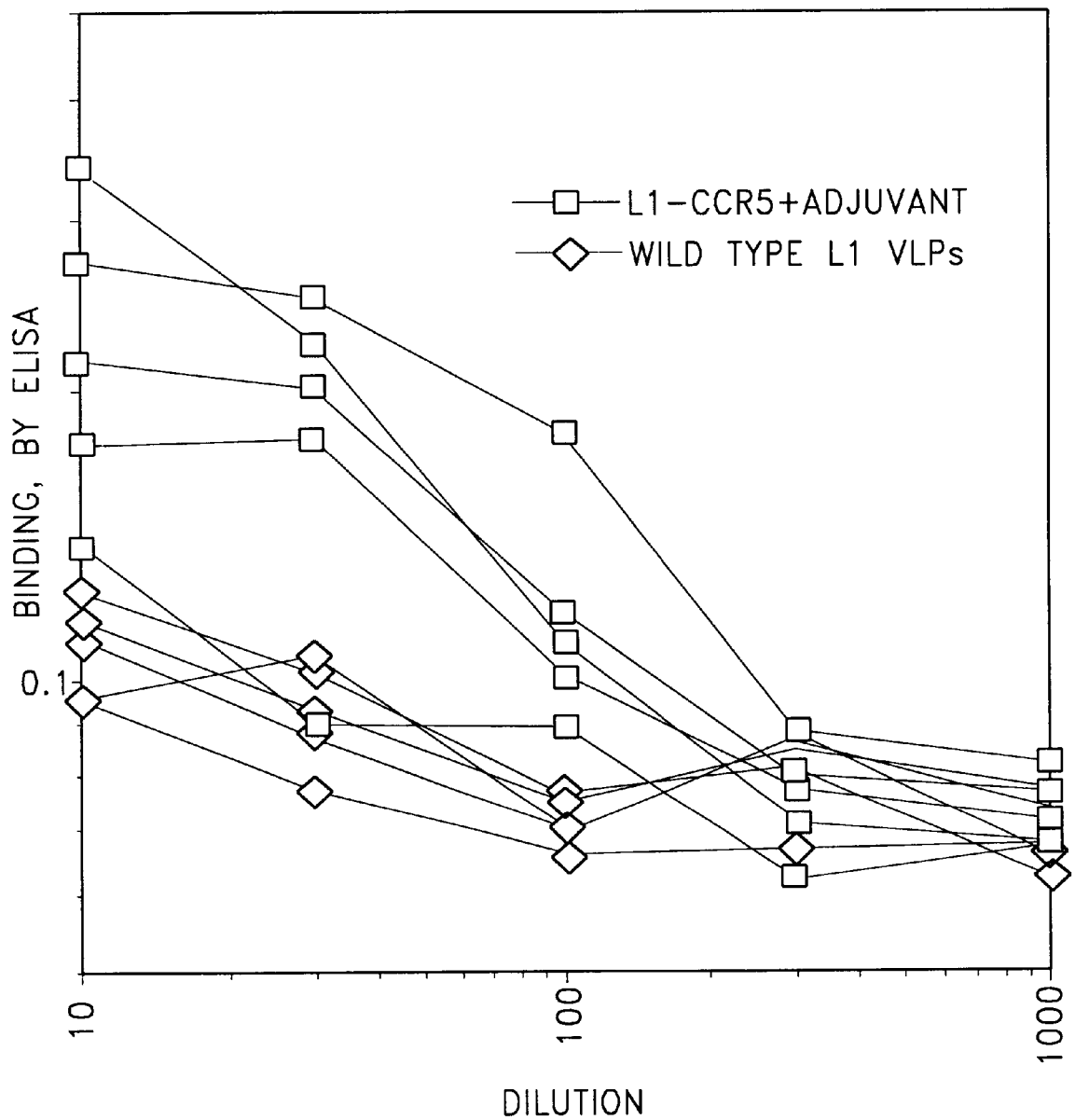
FIG. 5 is a line graph that shows primate serum antibody reactivity in an ELISA assay. Symbols represent results using sera from macaques inoculated with L1-CCR5 particles with adjuvant (■) or wild-type BPV-1 VLPs in the absence of adjuvant (◊).
Figure 6:
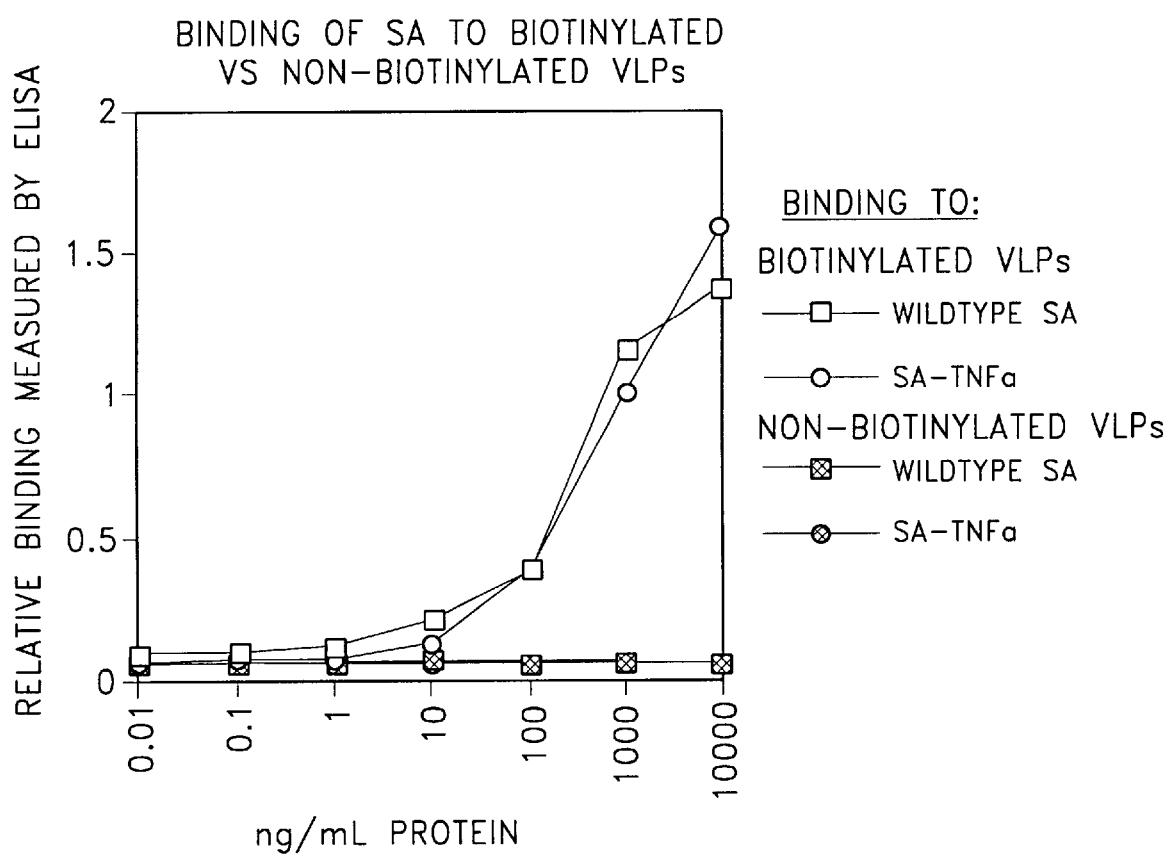
FIG. 6 is a line graph that shows the binding of streptavidin to biotinylated and non-biotinylated VLPs. Symbols represent (□) biotinylated VLPs conjugated with wild type Streptavidin (SA), (○) biotinylated VLPs conjugated with SA-TNF-α, (■) Non-biotinylated VLPs conjugated with wild type SA, and (●) non-biotinylated VLPs conjugated with SA-TNF-α.
Figure 7:
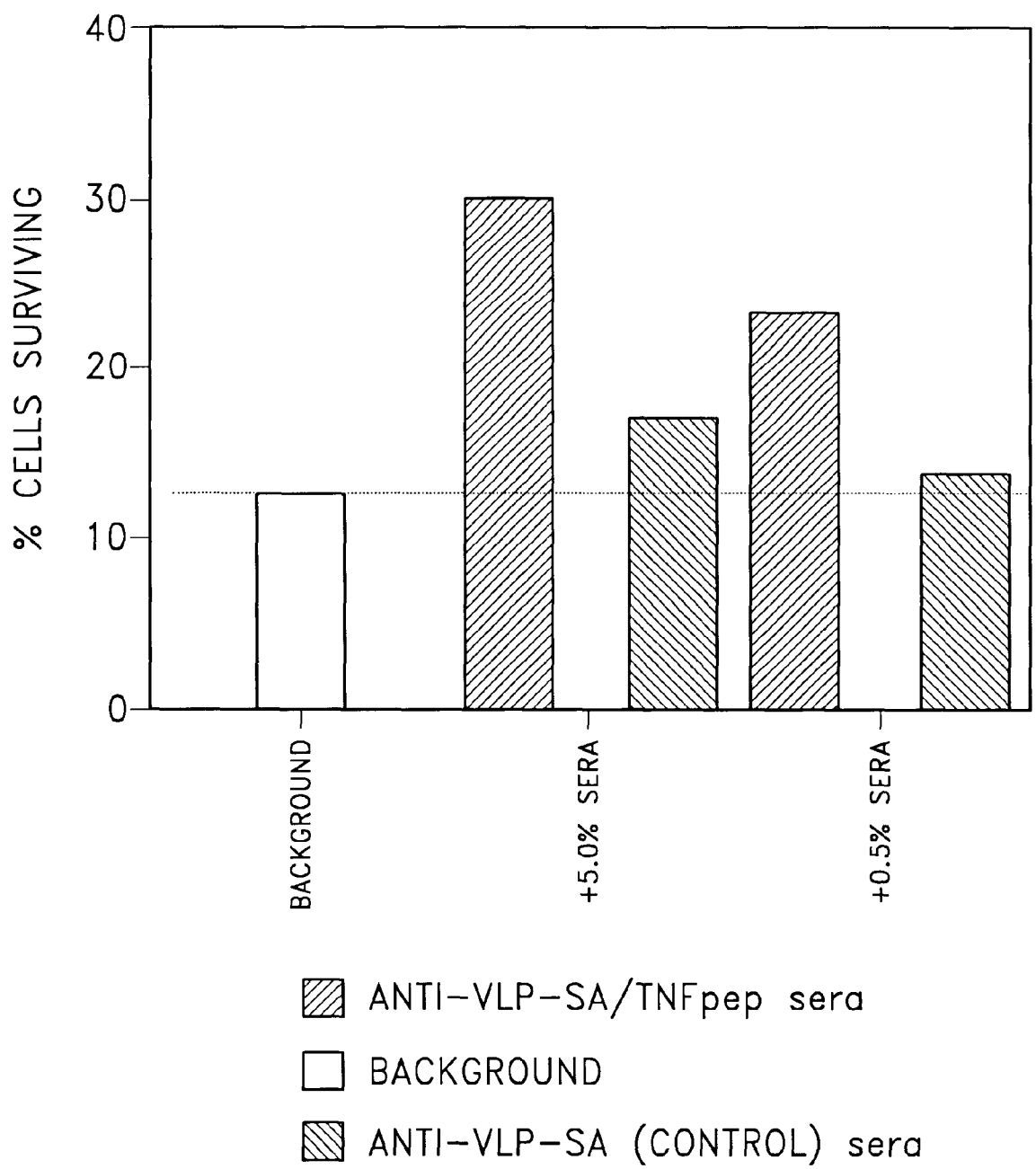
FIG. 7 is a bar graph that shows the results of a TNF-α cytotoxicity assay. Sera from mice inoculated with a streptavidin-TNF-α fusion protein (SA-TNF-α) joined to a biotinylated VLP was incubated with a TNF-α sensitive cell line (L929) in the presence of TNF-α. Sera from mice innoculated with streptavidin joined to biotinylated VLP was used as a control. The ability of the cells. Serum from SA-TNF-α inoculated mice (e.g., at a 5% concentration) demonstrated a three-fold increase in the number of surviving cells when compared to background levels.

Based on these results, sera from L1-CCR5 mice were tested for their ability to inhibit the infection of the M-tropic BaL strain of HIV-1, in a single replication cycle assay, using the MAGI indicator cell line. (Kimpton, J. & Emerman, M., *J. Virol.,* 66:2232–2239 (1992)). When indicator cells transiently transfected with HMHH were infected with HIV-1 BaL in the presence of L1-CCR5 sera, dilutions of 1:15, 1:30, and 1:75 exhibited 65%, 50%, and 45% neutralization, respectively, of infectivity (FIG. 4). At the same dilutions, control sera from wild type L1 VLP mice exhibited some non-specific neutralization, but it was only 25% at the 1:15 dilution and 15% at 1:30 and 1:75. In comparison, indicator cells infected with HIV-1 BaL in the presence of dilutions of hCCR5 binding monoclonal antibody (mAB182) (at an initial concentration of 1 $\mu g/\mu l$) used as a positive control exhibited a similar neutralization curve (FIG. 5). The L1-CCR5 sera were also tested for neutralization activity against the T-cell tropic isolate HIV-1 LAI, and, as expected, failed to show any neutralization above background levels against this isolate.

One concern of auto-antibody induction is that such procedures may have deleterious long-term consequences for the immunized animal, possibly including uncontrolled antigenic stimulation from the native CCR5 protein. However, in three mice that were monitored over a six month period after L1-CCR5 particle inoculation, we observed a two-to eight-fold decrease in the titer of CCR5-specific antibodies over this period; this decline was roughly equivalent to a parallel decline in the titer of L1-specific antibodies. Two of the animals exhibited two-fold declines in anti-CCR5 antibody titers and three-fold declines in anti-L1 antibody titers. The third animal exhibited an eight-fold decline in its anti-CCR5 titer and a ten-fold decline in its anti-L1 antibody titer. These results provide evidence that continued exposure to native CCR5 does not lead to continuous B cell induction, presumably because the cellular protein remains in a context that is ignored by the immune system, and, moreover, because the anti-CCR5 response depends exclusively on exposure to the CCR5 peptide on L1-CCR5 particles. The immunized mice maintained the same weight as control mice, and autopsies performed on two of the mice six months after the final boost did not reveal any gross pathological changes.

In humans, CCR5 is expressed predominantly on memory T cells ($CD3^+$, $CD4^+$, $CD26^{hi}$). Additionally, from 1 to 10% of macrophages in the thymus, spleen and lymph nodes express CCR5. (Zhang, L. et al., *J. Virol.,* 72:5035–5045 (1998)). FACS analysis of mouse mononuclear cells from spleen, thymus, and peripheral blood indicated that there was no decline in spleen or peripheral blood macrophage and T cell subsets that express CCR5 compared to control mice. Thus, according to our analysis, the mice immunized with L1-CCR5 particles did not suffer gross pathological changes over the period of observation.

More evidence supporting the benefits of using chimeric VLPs for breaking B cell tolerance in humans and specifically for the treatment and prevention of HIV infection, was obtained from primate studies in which auto-antibodies to a macaque CCR5 polypeptide were produced. (See Example 7). In these experiments, a recombinant expression construct encoding a macaque L1-CCR5 fusion protein was made. We cloned the corresponding human/macaque CCR5 peptide (they are the same) into the identical place in the L1 major capsid protein as used in the mouse experiments. Next we assessed capsid particle self assembly. When compared to our previous experiments with mouse L1-CCR5, particle formation was inefficient with the chimeric macaque L1-CCR5. Nevertheless, we were able to purify sufficient particles to immunize pig tail macaques. Four of the five animals that were vaccinated three times with the preparation, in the presence of Titer Max adjuvant, clearly produced CCR5 specific antibodies as measured in an ELISA assay (FIG. 5). We believe that a better VLP-based immunogen for generating auto-antibodies to human/macaque CCR5 can be generated by finding another site for insertion of the CCR5 peptide that would both display the foreign peptide on the VLP surface and would be more compatible with self assembly. Additionally, as described below, we believe that conjugated VLPs having the human/macaque CCR5 tolerogen will induce a better immune response.

The results from the first group of experiments demonstrate that incorporation of a peptide from the EC portion of a central antigen, mCCR5, into the regular array of a papillomavirus particle, followed by immunization of these particles, can induce auto-antibodies that bind to the receptor and block ligand and HIV-1 binding. Auto-antibodies to mCCR5 declined over time at a rate that was similar to the decline in L1 specific antibodies, suggesting that B cell stimulation by endogenous cell-surface CCR5 was not induced.

The anti-self antibodies induced by L1-CCR5 particles efficiently bound mCCR5 expressed on the cell surface, indicating that they function as true auto-antibodies. In contrast, antibodies induced by KLH-coupled CCR5 peptide failed to bind to native mCCR5. It is likely that binding auto-antibodies do not just recognize this particular amino acid sequence, but the tolerogen sequence in its native conformation. Moreover, the IgG from L1-CCR5 immunized mice block binding of a CCR5 ligand and inhibit HIV-1 infection via a chimeric CCR5 protein that contains the mouse CCR5 peptide, further demonstrating the specificity of these auto-antibodies and the therapeutic usefulness of aspects of the invention. The inhibition observed in these assays, was consistent, reproducible, specific, and similar to a control monoclonal antibody against the second EC loop of human CCR5.

The first EC loop of mCCR5 was chosen for our initial investigations because it allowed us to simultaneously test our approach to breaking B cell tolerance and provide a novel method to induce the body of a subject to inhibit HIV-1 infection. Because HIV-1 infected individuals who are heterozygous for an inactive CCR5 allele have delayed progression to AIDS, even partial reduction in CCR5 expression can have clinically significant effects. (Liu, R. et al., Cell, 86:367–77 (1996); Samson, M. et al., Nature (London), 382:722–5 (1996); Winkler, C. et al., Science, 279:389–93 (1998)). Our results also demonstrate that primates have the capacity to produce antibodies specific for CCR5 provided that the antigen is presented in an appropriate immunogen.

We observed no adverse effects of auto-antibody induction in mice that were followed for six months from the initial inoculation. While we did not test for auto-reactive T cells, we would not expect to break T cell tolerance to CCR5. T cells that recognize central auto-antigens are strongly selected against during the development of the immune system. Presumably the T cell help needed for immunoglobulin class switching to produce anti-CCR5 IgG is directed against the linked viral protein. Conversely, in adult animals there is a continuous generation of antibodies with new specificities as a result of RAG reactivation and peripheral editing of B cell receptor genes. (Han, S. et al., Science, 278:301–5 (1998); Papavasiliou, F. et al., Science, 278:298–301 (1998); Hertz, M. et al., Nature, 394:292–5 (1998)).

A Conjugated VLP That Breaks Immune Tolerance and Inhibits TNF-α Activity

Our second approach to break B cell tolerance involves the use of conjugated VLPs constructed by the addition of tolerogens to the outer surface of pre-formed VLPs. Once assembled, VLPs and capsomeric structures are quite stable and the addition of large or small tolerogens can be easily accomplished. In contrast to the chimeric VLP approach, wherein the size of the tolerogen is usually small because of the perturbation of self assembly, the conjugated VLP approach allows for the assembly of larger tolerogens to the VLP, which would provide more antibody epitopes and thus a more diverse set of auto antibodies. This strategy might also be applicable to polypeptides of more varied sequence and size than would genetic insertion of the sequences into the major capsid protein.

In our first experiments using the conjugated VLP approach, we joined the tolerogen TNF-α to VLPs by way of a biotin-streptavidin interaction. L1 VLPs were shown to be heavily biotinylated using sulfo-NHS-biotin (Pierce), which biotinylates exposed lysine residues. Under saturating conditions, the biotinylated VLPs bound streptavidin at a ratio of approximately three streptavidin tetramers per one L1 molecule. This result provided evidence that a streptavidin/tolerogen fusion protein could be presented to the immune system as a dense, ordered, and closely packed array of epitopes.

Accordingly, in *E. coli*, we generated a fusion protein comprising the streptavidin core linked to a twenty amino acid long fragment of mouse TNF-α, referred to as SA-TNF-α. The fusion protein was purified as insoluble inclusion bodies, solubilized in guanidine-HCl, and refolded by dialysis into physiologic buffer. The refolded fusion protein was then bound to biotinylated L1 VLPs, prepared as described above, so as to create the SA-TNF-α/VLP immunogen. The SA-TNF-α fusion protein bound to biotinylated VLPs with high occupancy (FIG. 6). Next, the SA-TNF-α/VLP immunogen was injected into mice so as to elicit an autoantibody response. Two injections of the conjugated VLPs into mice (3×5 μg) induced high titers of antibodies that bound native mouse TNF-α in an ELISA (See Table 1). In contrast, immunization with either SA-TNF-α alone or VLP alone failed to elicit a consistent or high autoantibody response. (See Tables 2 and 3). After a third injection of SA-TNF-α/VLP, titers of TNF-α antibodies reached $10^5$ in all mice.

TABLE 1

| Mouse titers after two immunizations with SA-TNFα protein coupled to biotinylated VLPs SA-TNF-α/VLP | | | | | |
|---|---|---|---|---|---|
| +Adjuvant | | | −Adjuvant | | |
| $10^4$ | $10^4$ | $10^4$ | 40 | 160 | 160 |

TABLE 2

| Mouse titers after two immunizations with SA-TNFα protein alone SA-TNFα | | | | | |
|---|---|---|---|---|---|
| +Adjuvant | | | −Adjuvant | | |
| $10^2$ | <10 | <10 | 10 | <10 | <10 |

Mouse titers after two immunizations with VLPs alone

TABLE 3

| Mouse titers after two immunizations with VLPs alone VLPs | | |
|---|---|---|
| +Adjuvant | | −Adjuvant |
| <10 | <10 | <10 |

These results established that the SA-TNF-α/VLP immunogen efficiently broke B cell tolerance. More evidence that the conjugated VLP effectively broke B cell tolerance was obtained from TNF-α cytotoxicity assays. In these experiments, the ability of the SA-TNF-α/VLP immunogen to prevent TNF-α mediated apoptosis of an indicator cell line (L929 cells) was determined. Sera obtained from mice innoculated with either streptavidin bound VLPs (controls) or SA-TNF-α/VLPs was incubated with TNF-α and the sera treated or non-sera treated TNF-α samples were added to cells in culture. The ability of the sera to neutralize TNF-α activity was measured by an increase in the percentage of surviving cells. Sera from the SA-TNF-α/VLP innoculated mice (at a 5% solution) lead to a three-fold increase in cell survival over background levels (FIG. 7). Given the encouraging results with the mouse TNF-α fusion proteins, we made similar streptavidin fusion proteins for each of the four extracellular domains of macaque CCR5. All four fusion proteins have been generated and purified from *E. coli* inclusion bodies. We have been able to refold three of the four such that they strongly bind biotinylated VLPs.

As shown in the discussion above and the following examples, a peptide sequence corresponding to a tolerogen can abrogate B cell tolerance to the native protein, when presented in the context of a highly organized array of assembled chimeric or conjugated viral capsomeres. The ability to abrogate B cell tolerance using the procedures described herein has numerous applications. For example, this technique can be used to generate mouse anti-self monoclonal antibodies. Additionally, this approach is effective as a means of modulating the activity of a soluble protein in order to examine its function in normal or disease processes in experimental animal models. Moreover, induction of auto-antibodies provides an effective alternative to monoclonal antibody therapy for human disease, such as in the treatment of breast cancer and rheumatoid arthritis with antibodies directed against ErbB-2 and TNF-α, respectively (Maini et al., *Immunol. Rev.*, 144:195 (1995); Baselga et al., *J. Clin. Oncol,* 14:737 (1996)). The discussion below describes more aspects that concern embodiments of the invention.

Supports and Capsomeric Structures

While virus-like particles or capsomeric structures represent a preferred system for delivering self peptides to the immune system to stimulate production of auto-antibodies, we also intend for the invention to embrace other structured assemblages that can present a tolerogen in an ordered, closely spaced repetitive array. These supports have an ordered assembly of subunits and allow for at least one B cell epitope of a tolerogen to be joined to the support in a regular, repetitive array. Preferably, the supports and capsomeric structures are capable of presenting antigen with spacing of about 10–500 angstroms, advantageously about 50–300 angstroms, and preferably about 100 angstroms. That is, spacing between presented antigen molecules can be greater than or equal to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 210, 201, 202, 203, 204, 205, 206, 207, 208, 209, 210, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 angstroms. Modified T-independent type 2 antigens (TI-2) may behave like VLPs in this regard. These include pneumococcal polysaccharide, Salmonella polymerized flagellin, dextran and hapten-conjugated ficol (polysucrose).

Although virus-like particles of papillomavirus have been employed in the exemplary demonstration presented herein, virus-like particles of other papillomaviruses and non-papillomaviruses also are contemplated for use in stimulating production of autoantibodies. Infectious virus are also envisioned. Attenuated or inherently non-pathogenic viruses can be modified in a similar fashion and used to generate autoantibodies. Examples of chimeric VLPs particularly contemplated for use in connection with the invention are those described in *Intervirology,* 39:1 (1996), herein incorporated by reference. Among the chimeric VLPs contemplated for use in stimulating production of autoantibodies are: BPV-1, HPV-1, HPV-6, HPV-11, HPV-16, HPV-18, HPV-33, HPV-45, CRPV, and COPV. Also contemplated are: B19 parvovinis, Hepatitis B virus core particles, Hepatitis B surface antigen particles, HIV gag particles, Tobacco Mosaic Virus, Cowpea mosaic virus, Yeast Ty particles, and RNA phage. Virus-like particles have been made, and chimeric VLPs can be made for SV40, Polyomavirus, Adenovirus, Herpes Simplex, Rotavirus, and Norwalk Virus. Notably, workers in the art have already determined the complete nucleotide sequence of the entire genomes of many papillomavirus, including: BPV-1, BPV-2, BPV-4, CRPV, DPV, EPV, HPV-1, HPV-5, HPV-6, HPV-8, HPV-11, HPV-16, HPV-18, HPV-31, HPV-33 and RhPV. Preferred capsid proteins that are used to construct the capsomeric structures of embodiments of the invention, however, include proteins from icosohedral viruses or viruses that have a natural mammalian reservoir host. Thus, polynucleotide sequences encoding many different major and minor coat proteins that can be used in connection with the methods described herein already are known.

It is to be understood that VLPs that include major and/or minor coat proteins can be used to prepare immunogenic compositions according to the methods disclosed herein. In the particular case of the papillomavirus L2 minor coat protein, it is to be understood that L2 chimeras may expose the inserted antigen on the surface. The target antigens are external. An L2/E7 fusion that we have used to generate papillomavirus E7 antibodies, when incorporated in VLPs, has the first 110 amino acids of BPV L2 fused to the entire HPV16 E7 polypeptide sequence. (Lowy et al., U.S. Pat. No. 5,618,536 herein incorporated by reference.) In this instance, the E7 sequence was fused to a site of L2 that had previously been shown to correspond to a virus-neutralizing epitope (Roden, et al., *J. Virol,* 68:7570 (1994)). In the disclosure below, several approaches to join tolerogens to the ordered assemblages of the invention are provided.

Approaches to Make Supports or Capsomeric Structures That Present Tolerogens

As discussed above, in general, two different approaches can be employed to incorporate tolerogens into the structures of virus-like particles. By one approach, there first is created a genetic construct that encodes an amino acid sequence including both virus coat protein sequences and the self peptide sequence of interest. The resulting construct encodes a single chimeric polypeptide that displays the self peptide on an outer surface of a particle following self-assembly of the hybrid coat protein to form capsomeric structures or VLPs. According to the second approach, the self peptide displayed on the outer surface of the VLP is linked directly or indirectly to a plurality of subunit proteins that comprise a preformed VLP. For example, wild type papillomavirus L1 protein can be a recombinant coat protein coupled to a first binding agent having an association constant for a second binding agent ranging from $10^7$–$10^{10}$, from $10^4$–$10^8$, from $10^{10}$–$10^{12}$, or from $10^{12}$–$10^{16}$. The second binding agent can be adapted for coupling to the self peptide. In a particularly preferred embodiment of the invention, biotinylated wild type VLPs are first produced. This can be accomplished by biotinylating preformed VLPs. Next, the biotinylated VLPs are combined with an avidin-or streptavidin-linked self polypeptide to form complexes having surfaces whereon the self peptide is displayed. In this fashion multiple copies of the self peptide are indirectly coupled to the VLP such that the self peptide is not integrated into the peptide backbone of the coat protein. Thus, compositions that include a hybrid coat protein linked to a self peptide, either as an integral part of the hybrid coat protein polypeptide sequence or indirectly, such as through a biotin linkage, are intended to fall within the scope of the invention.

Embodiments of the invention desirably provide tolerogens in such a form or in such a way that a sufficient affinity, abrogation of B cell tolerance or inhibition of a disease state (e.g., viral infection, neoplasis, or inflammation) is achieved. While a natural monomeric tolerogen (that is, a tolerogen that presents a discrete molecule, thus, carrying only a small number of epitopes) can be sufficient to achieve a desired response, a synthetic tolerogen or a multimeric immunogen (e.g., a VLP presenting multiple molecules of the tolerogen, thus, having a greater number of the same epitopes) often times can elicit a greater immune response. It should be noted that the term "multimeric" refers to the presence of more than one identical molecule on a support or capsomeric structure. For example, several identical molecules of CCR5 or fragments thereof displayed on a VLP. The term multimeric should be distinguished from the term "multimerized", which refers to a support or capsomeric structure joined to hybrid molecules, wherein each hybrid molecule comprises multiple copies of the tolerogen or individual epitopes thereof joined in tandem. For example, each individual multimerized tolerogen can comprise a twenty amino acid long fragment of CCR5 that is randomly repeated with or without interspersed linkers (e.g., λ phage linkers) and a plurality of multimeric tolerogens can be joined to a support or capsomeric structure so as to form a multimerized/multimeric immunogen.

A multimeric immunogen (synthetic or natural) that effectively breaks B cell tolerance can be obtained by joining tolerogens to a support or a capsomeric structure. Supports suitable for this purpose include, but are not limited to, polyacrylamide beads, agarose beads, polystyrene beads, magnetic beads, latex particles, carbohydrate assemblies (e.g., oligosaccharide-based beads or assemblies), lipid assemblies (e.g., lipid membranes), protein assemblies or polymers (e.g., poly-L-lysine or poly-D, L-alanine) and other supports known in the art to have an organized, symmetrical assembly of subunits. Inorganic carriers, such as silicon oxide material (e.g. silica gel, zeolite, diatomaceous earth or aminated glass) to which the tolerogen is covalently linked through a hydroxy, carboxy or amino group and a reactive group on the carrier can also be used with some embodiments.

In several embodiments, the tolerogen is joined to the support or capsomeric structure by way of a linker, which can be a bond between two chemically reactive species, a ligand/receptor interaction, or a peptide that has been joined to the tolerogen so as to allow for attachment to the support or capsomeric structure or to provide greater freedom of association of the tolerogen with a cell of the immune system. In some embodiments, for example, the support or capsomeric structure has a hydrophobic surface that interacts with a portion of the tolerogen by a hydrophobic non-covalent interaction. In some cases, the hydrophobic surface of the support is a polymer such as plastic or any other polymer in which hydrophobic groups have been linked such as polystyrene, polyethylene or polyvinyl.

Additionally, the tolerogen can be covalently bound to a support or capsomeric structure including proteins and oligo/polysaccharides (e.g. cellulose, starch, glycogen, chitosane or aminated sepharose). In these later embodiments, a reactive group on a tolerogen, such as a hydroxy or an amino group, is used to join to a reactive group on the support or capsomeric structure so as to create the covalent bond. Embodiments can also comprise a support with a charged surface that interacts with the tolerogen. Additional embodiments comprise a support that has other reactive groups that are chemically activated so as to attach a tolerogen. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

In other embodiments, the interaction of biotin with avidin-like molecules (e.g., streptavidin and neutraavidin) is exploited. As presented earlier, VLPs can be biotinylated and can be easily joined to tolerogen/streptavidin fusion proteins. By inserting more lysine or cysteine molecules in capsid proteins, greater biotinylation can be achieved and, thus, more tolerogen can be added to the surface of a VLP. Further, by using site-specific mutagenesis techniques, lysine or cysteine molecules can be strategically inserted so as to establish a VLP having a dense and highly organized repetitive array of tolerogens. As one of skill will immediately appreciate, the converse also can be performed, that is, the use of streptavidin/capsid protein fusions and biotinylated tolerogens. In another embodiment, λ linkers of an appropriate length are inserted between the tolerogen and the support or capsomeric structure so as to encourage greater flexibility and overcome any steric hindrance that can be present. The determination of an appropriate length of linker that allows for an optimal immune response can be made by screening the tolerogen with varying linkers in the various assays described herein A composite support having more than one type of tolerogen is also an embodiment. A "composite support" can be a macromolecular structure used to join or immobilize two or more different tolerogens. The composite supports are also constructed by utilizing hydrophobic interactions and covalent linkages formed through reactive groups, as detailed above. Further, linkers, such as λ linkers, of an appropriate length between the tolerogens and the support are inserted in some embodiments so as to encourage greater flexibility in the molecule and overcome steric hindrance. The determination of an appropriate length of linker that allows for an optimal immune response can be made by screening the tolerogens with varying linkers in the assays detailed in the present disclosure.

In other embodiments of the present invention, the multimeric and composite supports discussed above have attached multimerized tolerogens so as to create a "multimerized-multimeric support" and a "multimerized-composite support", respectively. An embodiment of a multimerized tolerogen, for example, is obtained by creating an expression construct having two or more nucleotide sequences encoding a tolerogen joined together by using conventional techniques in molecular biology. The expressed fusion protein is one embodiment of a multimerized agent and is then joined to a support. A support having many such multimerized agents is termed a multimerized-multimeric support. The multimerized form of a tolerogen can be advantageous for many applications because of the ability to obtain an agent with a better ability to induce an immune response and, thus, break B cell tolerance. The incorporation of linkers or spacers, such as flexible λ linkers, between the protein domains that make-up the multimerized agent can also be advantageous for some embodiments. The insertion of λ linkers of an appropriate length between protein binding domains, for example, encourages greater flexibility in the molecule and overcomes steric hindrance between the domains. Similarly, the insertion of linkers between the multimerized tolerogens and the support encourages greater flexibility and reduces steric hindrance presented by the support or capsomeric structure. The determination of an appropriate length of linker that allows for an optimal immune response can be accomplished by screening the tolerogens with varying linkers in the assays detailed in this disclosure. In a similar fashion composite-multimerized-multimeric supports with and without linkers can be constructed by joining more than one different multimerized tolerogen to a support.

Particularly preferred sites on virus-like particles for inserting self antigens against which an autoimmune response is desired are virus-neutralizing epitopes. This is because virus-neutralizing epitopes typically are disposed on the surface of the virus and are available for antibody binding. These features are desirable for presenting self antigens to the immune system in the structural context of a chimeric virus-like particle. Methods for identifying papillomavirus neutralizing epitopes have been described by Ludmerer et al., in *J. Virol,* 70:4791 (1997); Ludmerer et al., in *J. Virol.,* 71:3834 (1997); and by Roden et al., in *J. Virol.,* 71:6247 (1997). Generally, methods for identifying virus-neutralizing epitopes can employ a monoclonal antibody that preferentially binds to one of two closely related L1 proteins and then systematically making recombinants that reassort the specific amino acid differences between them. Alternatively, the polypeptide sequences encoding the L1 proteins of related viruses, for example papillomaviruses, can be aligned to identify segments that are most varied in length. These highly variable positions likely will be external or internal loops of the capsid protein. The external loops will be candidates for substitution by polypeptide sequences of self antigens for which an autoimmune response is sought. Thus, virus-neutralizing epitopes, as can readily be identified using routine laboratory procedures, are preferred sites for disposition of self peptides in the VLPs or capsomeric structures of the invention. For example, the site of a virus-neutralizing epitope on BPV-1 would be a preferred site on a corresponding VLP for disposition of a self peptide. In the section below, a discussion of the size of tolerogens that can be used with aspects of the invention is provided.

Size of Tolerogen on the Support or Capsomeric Structure

Generally, the number of amino acids representing the antigen that is incorporated into the structure of the viral coat protein or joined to the support or capsomeric structure must be large enough to correspond to an epitope that is characteristic of the antigen and that can fit into the antigen binding site of an antibody. Since it is generally accepted that a linear arrangement of 5 to 6 amino acids is sufficient to bind to an antigen binding site, it is preferred that at least 5 amino acids of the self antigen are incorporated into the structure of the immunogen. However, it is to be understood that a greater number of amino acids can also be used with good results. In the Example presented herein, 16 amino acids of the mouse CCR5 protein were introduced into the structure of an L1 major coat protein with good results. Longer polypeptide sequences representing tolerogens are also contemplated for integration into the structure of the viral coat for use as immunogens for inducing anti-self immune reactions. Thus, it is preferred that the immunogenic virus-like particle incorporate self polypeptide sequences at least 5 amino acids in length but the length of tolerogen may be greater than 200 amino acids and may include a full-length protein. A desirable range is from 5 to 200 amino acids. That is, the tolerogen can be greater than or equal to 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 amino acids in length.

It is contemplated that biotinylated VLPs will be capable of complexing with, and presenting to the immune system, peptides that are substantially longer than 16 amino acids in length. It is also possible to incorporate into the structure of a hybrid minor coat protein a polypeptide sequence representing a full length protein. Below we describe the wide variety of tolerogens that can be presented as an embodiment of the invention.

Many Types of Tolerogens Can Be Presented On a Support or Capsomeric Structure

The invention can be practiced using a wide variety of tolerogens. In preferred embodiments, the tolerogens are self antigens. Preferred self antigens include those for which antibodies targeted against that self antigen has been shown to be an effective therapeutic agent. In general, the self antigen will correspond to a self antigen of the organism that is immunized with the composition that includes the self antigen linked to the VLP. Thus, the sequence of a human self peptide, such as the human CCR5 chemokine receptor, can be introduced into the structure of a VLP for use in immunizing humans. In this way humans can be made to produce autoantibodies. Particular examples of self antigens that can be used are central self antigens such as TNF-α and CTLA-4.

TNF-α has been implicated in a number of human diseases, most notably as the principle soluble effector in rheumatoid arthritis (RA). (Maini et al., *Imm. Reviews,* 144:195 (1995)). Rheumatoid arthritis is a chronic and painful disease of multiple joints which is thought to affect around 1% of people worldwide. The symptoms of RA are ineffectively treated with drug therapy. This has prompted a desire to develop alternative therapeutic strategies that target the effectors of the disease rather than the symptoms. Anti-TNF-α monoclonal antibody therapy has produced dramatic improvement in both objective and subjective measures of RA in human clinical trials (Feldman et al., *Annu. Rev. Immunol.*, 14:397 (1996)). Unfortunately, the benefits have proven to be transient and this loss of effectiveness has correlated with the development of antibodies against the monoclonal antibody. Coupled with the fact that TNF-α is a small soluble protein that is biologically active at relatively low serum concentrations, these observations make TNF-α an attractive target for an autoantibody inducing vaccine. Furthermore, there is a good mouse model for TNF-α mediated RA in which to test the concept (Thorbecke et al., *Proc. Natl. Acad. Sci. USA*, 89:7375 (1992)).

CTLA-4 is a membrane bound receptor of T cells that appears to be an important regulator of B7 mediated co-stimulation of T cells (Thompson et al., *Immunity*, 7:445 (1997)). Costimulation is critical for generating an effective CD8+ T cell mediated cytotoxic T lymphocyte (CTL) responses. Whether CTLA-4 normally acts to transmit positive or negative signals after B7 engagement is currently unresolved (Zheng et al., *Proc. Natl. Acad. Sci. USA*, 95:6284 (1998)). However, antibodies to CTLA-4 clearly potentiate the generation of CTLs in response to tumor antigens in mouse tumor models. Thus, a vaccine for inducing autoantibodies to CTLA-4 could be used to augment the immune response to tumors either alone or in combination with tumor antigen specific vaccines (Leach et al., *Science*, 271:1734 (1996)). Notably, transient autoimmune disease symptoms may be acceptable side-effects in patients having widely disseminated or inoperable cancers that are unresponsive to conventional therapies.

Other contemplated tolerogens include viral antigens from viruses that chronically infect humans including, but not limited to, Hepatitis C virus (HCV), Hepatitis B virus (HBV), and HIV, chemokines, and molecules associated with neoplasia and angiogenesis. By using the teachings described herein, one of skill in the art can present a variety of different tolerogens, including, nucleic acids, peptides, lipids, and carbohydrates, on biotinylated VLPs. For example, a sandwich approach can be employed in which a biotinylated nucleic acid is first bound to streptavidin and then the nucleic acid/streptavidin complex is bound to a biotinylated VLP. Similarly, using conventional chemistry, lipids can be joined to biotin, bound to streptavidin and bound to biotinylated VLPs.

The ability to break B cell tolerance to small organic compounds was established while performing experiments on biotinylated VLPs. Biotin is a vitamin and a self tolerogen in mice. We prepared biotinylated VLPs, as described earlier, and injected these immunogens into mice as before. The presence of anti-Biotin antibodies was determined by an ELISA assay in which biotinylated BSA was used as the target antigen. As a negative control, the sera reactivity to unbiotinylated BSA was determined. The anti-biotin antibodies in the sera of three mice at titers of was 100, 100, and 10 and no reactivity to the unbiotinylated BSA was detected.

The compositions described above can be used as biotechnological tools, for example binding to an isolated cell of the immune system, which can provide a model system for the study of B cell tolerance but are preferably incorporated into therapeutics and prophylactic pharmaceuticals for the treatment and prevention of human disease. The disclosure below discusses several of the therapeutic and prophylactic embodiments of the invention.

Therapeutic and Prophylactic Applications

The compositions of the invention are suitable for treatment of subjects either as a preventive measure to avoid diseases such as cancer, viral infection or inflammatory conditions or as a therapeutic to treat subjects already afflicted with these maladies. Although anyone could be treated with the agents of the invention as a prophylactic, the most suitable subjects are people at risk for diseases with mediators accessible to Ab binding.

The pharmacologically active compounds of this invention can be processed in accordance with conventional methods of galenic pharmacy to produce medicinal agents for administration to patients, e.g., mammals including humans. They can be incorporated into a pharmaceutical product with and without modification. Further, the manufacture of pharmaceuticals or therapeutic agents that deliver the immunogens of the invention by several routes are aspects of the invention.

The compounds of this invention can be employed in admixture with conventional excipients, i.e., pharmaceutically acceptable organic or inorganic carrier substances suitable for parenteral, enteral (e.g., oral) or topical application that do not deleteriously react with the compositions of the invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular formulation can vary based on the individual patient and the stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, ED50/LD50. Pharmaceutical compositions that exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors that may be taken into account include the severity of the disease, age, and weight of the patient; diet, time and frequency of administration, drug combination(s), reaction sensitivities, and tolerance/response to therapy.

Routes of administration include, but are not limited to, transdermal, parenteral, gastrointestinal, transbronchial, and transalveolar. Parenteral routes of administration include, but are not limited to, electrical or direct injection such as direct injection into a central venous line, intravenous, intramuscular, intraperitoneal or subcutaneous injection. Gastrointestinal routes of administration include, but are not limited to, ingestion and rectal. Transbronchial and transalveolar routes of administration include, but are not limited to, inhalation, either via the mouth or intranasally.

Compositions suitable for transdermal administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, or subcutaneous injection.

Compositions suitable for transbronchial and transalveolar administration include, but not limited to, various types of aerosols for inhalation. Devices suitable for transbronchial and transalveolar administration are also embodiments. Such devices include, but are not limited to, atomizers and vaporizers. Many forms of currently available atomizers and vaporizers can be readily adapted to deliver the compositions of the invention.

Compositions suitable for gastrointestinal administration include, but not limited to, pharmaceutically acceptable powders, pills or liquids for ingestion and suppositories for rectal administration. Due to the ease of use, gastrointestinal administration, particularly oral, is the preferred embodiment of the present invention.

Several methods of treatment and prevention of human diseases are provided, which involve administration of the pharmaceutical embodiments of the invention. In these aspects, compositions of the invention are incorporated into pharmaceuticals and are administered to patients in need. By one approach, a subject at risk for contracting HIV infection or another chronic viral infection or a subject already infected with HIV or another chronic viral infection is identified by conventional diagnostic assays and then a therapeutically or prophylactically beneficial amount of a pharmaceutical of the invention is administered to the subject. A similar approach can be employed to treat and/or prevent chronic inflammatory disease. That is identifying a subject in need and then administering a pharmaceutical comprising a composition of the invention. Other methods of the invention include an approach to raise high titer neutralizing antibodies. Accordingly, agents (e.g., a composition of the invention) are identified for their ability to break B cell tolerance and are subsequently administered to a subject in need. Additional embodiments include a method to make monoclonal and polyclonal antibodies to a composition of the invention. These novel antibodies can also be incorporated into pharmaceuticals and administered to patients in need for the treatment and prevention of human disease. The disclosure below provides more discussion of these approaches.

Preparation of Antibodies to Chimeric and Conjugated VLPs

Following construction of a chimeric or conjugated VLP, these compositions can be used to generate antibodies. (See Example 10). Antibodies that recognize a chimeric or conjugated VLP have many uses including, but not limited to, biotechnological applications, therapeutic/prophylactic applications, and diagnostic applications. Such antibodies include, but are not limited to, polyclonal, monoclonal, chimeric, single chain, Fab fragments and fragments produced by a Fab expression library. Neutralizing antibodies, i.e., those that inhibit CCR5-mediated adhesion, are especially preferred for therapeutics.

For the production of antibodies, various hosts including goats, rabbits, rats, mice, etc. can be immunized by injection with a chimeric or conjugated VLP. Depending on the host species, various adjuvants can be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (Bacillus Calmette-Guerin) and Corynebacterium parvum are potentially useful adjuvants. However, VLP-based immunogens can also increase the titer of antibodies to tolerogens without the addition of adjuvants.

Monoclonal antibodies to a chimeric or conjugated VLP can be prepared using any technique that provides for the production of antibody molecules by continuous cell lines in culture. These include but are not limited to the hybridoma technique originally described by Koehler and Milstein (*Nature*, 256:495–497 (1975), the human B-cell hybridoma technique (Kosbor et al., *Immunol Today*, 4:72 (1983); Cote et al., *Proc Natl Acad Sci*, 80:2026–2030 (1983), and the EBV-hybridoma technique Cole et al. *Monoclonal Antibodies and Cancer Therapy*, Alan R. Liss Inc, New York N.Y., pp 77–96 (1985), all articles herein incorporated by reference. In addition, techniques developed for the production of "chimeric antibodies", the splicing of mouse antibody genes to human antibody genes to obtain a molecule with appropriate antigen specificity and biological activity can be used. (Morrison et al., *Proc Natl Acad Sci*, 81:6851–6855 (1984); Neuberger et al., *Nature*, 312:604–608 (1984); and Takeda et al., *Nature*, 314:452–454 (1985), all articles herein incorporated by reference. Alternatively, techniques described for the production of single chain antibodies (U.S. Pat. No. 4,946,778) can be adapted to produce single chain antibodies directed to a chimeric or conjugated VLP, herein incorporated by reference. Antibodies can also be produced by inducing in vivo production in the lymphocyte population or by screening recombinant immunoglobulin libraries or panels of highly specific binding reagents as disclosed in Orlandi et al., *Proc Natl Acad Sci*, 86: 3833–3837 (1989), and Winter G. and Milstein C, *Nature*, 349:293–299 (1991), all articles herein incorporated by reference.

Antibody fragments that contain specific binding sites for a chimeric or conjugated VLP can also be generated. For example, such fragments include, but are not limited to, the $F(ab')_2$ fragments that can be produced by pepsin digestion of the antibody molecule and the Fab fragments that can be generated by reducing the disulfide bridges of the $F(ab')_2$ fragments. Alternatively, Fab expression libraries can be constructed to allow rapid and easy identification of monoclonal Fab fragments with the desired specificity. (Huse W. D. et al., *Science*, 256:1275–1281 (1989), herein incorporated by reference).

By one approach, monoclonal antibodies to a chimeric or conjugated VLP are made as follows. Briefly, a mouse is repetitively inoculated with a few micrograms of the selected protein or peptides derived therefrom over a period of a few weeks. The mouse is then sacrificed, and the antibody producing cells of the spleen isolated. The spleen cells are fused in the presence of polyethylene glycol with mouse myeloma cells, and the excess unfused cells destroyed by growth of the system on selective media comprising aminopterin (HAT media). The successfully fused cells are diluted and aliquots of the dilution placed in wells of a microtiter plate where growth of the culture is continued. Antibody-producing clones are identified by detection of antibody in the supernatant fluid of the wells by immunoassay procedures, such as ELISA, as originally described by Engvall, E., *Meth. Enzymol.,* 70:419 (1980), herein incorporated by reference, and derivative methods thereof. Selected positive clones can be expanded and their monoclonal antibody product harvested for use. Detailed procedures for monoclonal antibody production are described in Davis, L. et al. *Basic Methods in Molecular Biology* Elsevier, N.Y. Section 21-2.

Polyclonal antiserum containing antibodies to heterogenous epitopes of a single protein can be prepared by immunizing suitable animals with the expressed protein or peptides derived therefrom described above, which can be unmodified or modified to enhance immunogenicity. Effective polyclonal antibody production is affected by many factors related both to the antigen and the host species. Also, host animals vary in response to site of inoculations and dose, with both inadequate or excessive doses of antigen resulting in low titer antisera. Small doses (ng level) of antigen administered at multiple intradermal sites appears to be most reliable. An effective immunization protocol for rabbits can be found in Vaitukaitis, J. et al. *J. Clin. Endocrinol. Metab.,* 33:988–991 (1971).

Booster injections can be given at regular intervals, and antiserum harvested when antibody titer thereof, as determined semi-quantitatively, for example, by double immunodiffusion in agar against known concentrations of the antigen, begins to fall. See, for example, Ouchterlony, O. et al., Chap. 19 in: *Handbook of Experimental Immunology* D. Wier (ed) Blackwell (1973). Plateau concentration of antibody is usually in the range of 0.1 to 0.2 mg/ml of serum (about 12 µM). Affinity of the antisera for the antigen is determined by preparing competitive binding curves, as described, for example, by Fisher, D., Chap. 42 in: *Manual of Clinical Immunology,* 2d Ed. (Rose and Friedman, Eds.) Amer. Soc. For Microbiol., Washington, D.C. (1980). Antibody preparations prepared according to either protocol are useful in quantitative immunoassays that determine concentrations of antigen-bearing substances in biological samples; they are also used semi-quantitatively or qualitatively. Additionally, a chimeric or conjugated VLP can be used to induce antibody production in humans, as discussed throughout this disclosure. Accordingly, a chimeric or conjugated VLP can be joined to or administered with another protein, carrier, support, or adjuvant so as to generate a pharmaceutical or vaccine that will induce potent immune response.

The following Example describes the procedures that were used to prepare and express a polynucleotide encoding a chimeric L1-CCR5 protein that self assembled into capsomeric structures. The below-described procedure involved modifying an L1 encoding polynucleotide to incorporate an amino acid sequence encoding a CCR5 peptide fragment. In this exemplary demonstration, sixteen codons from the C57B1/6 (B6) mouse CCR5 (mCCR5) first extracellular loop were separately inserted into one of three regions of the BPV-1 L1 sequence corresponding to the sites of virus-neutralizing epitopes. The positions of these epitopes previously had been deduced by alignment of polypeptide sequences of various human papillomaviruses. The three non-contiguous regions of L1 that received the CCR5 sequence have been described by Ludmerer et al., *J. Virol,* 70:4791 (1996); by Ludmerer, et al., *J. Virol.,* 71:3834 (1997); and by Roden, et al., *J. Virol.,* 71:6247 (1997). Since the amino acids at these sites were likely to be expressed on the capsid surface, analogous sites in BPV-1 L1 were targeted for peptide insertion. This ensured that the portion of the chimeric L1 protein that included the CCR5 peptide sequence would be surface-expressed and available for efficient presentation to the humoral immune system.

Example 1 describes the method used to create a chimeric L1-CCR5 protein that self assembled into antigenic particles.

EXAMPLE 1

Construction of a Chimeric Protein Capable of Self Assembling into Antigenic Particles Polynucleotides encoding three different L1-CCR5 chimeras (designated "L1-CCR5 chimera 1", "L1-CCR5 chimera 2" and "L1-CCR5 chimera 3") were prepared by overlap extension PCR mutagenesis essentially according to the technique described by Ho et al., in *Gene,* 77:51 (1989). A polynucleotide encoding BPV-1 L1 (Chen et al., *Nature,* 299:557 (1982)) was cloned as an EcoRI/KpnI fragment into complementary sites of the multiple cloning site of the baculovirus pFastBac1 expression vector (Gibco BRL, Gaithersberg, Md.). Portions of the BPV-1 L1 sequence in each of the three chimeras were replaced by a sequence encoding the first extracellular loop of C57B1/6 mCCR5. The polypeptide sequence from the mCCR5 protein had the sequence: His-Tyr-Ala-Ala-Asn-Glu-Trp-Val-Phe-Gly-Asn-Ile-Met-Cys-Lys-Val (SEQ ID NO:1) (Boring et al., *J. Biol. Chem.,* 271:7551 (1996)). In L1-CCR5 chimera 1, the sequence encoding L1 amino acids 130–136 was replaced by the mCCR5 sequence. In L1-CCR5 chimera 2, the sequence encoding L1 amino acids 275–285 was replaced by the mCCR5 sequence. In L1-CCR5 chimera 3, the sequence encoding L1 amino acids 344–350 was replaced by the mCCR5 sequence. The final clones were verified by restriction digest analysis and by nucleotide sequence analysis of the PCR-amplified region.

Recombinant baculovirus stocks containing the genes coding for the chimeric L1-CCR5 proteins or wild type BPV-1 L1 were generated using the GIBCO BRL baculovirus system, as described by the manufacturer. Papillomavirus-like particles were purified from recombinant baculovirus-infected Sf9 cells as described previously. (Kimbauer, R. et al., *Proc. Natl. Acad. Sci. USA,* 89:12180–12184 (1992); Greenstone, H. L. et al., *Proc. Natl. Acad. Sci. USA,* 95:1800–1805 (1998)). The general morphology of the particle preparations was analyzed by mobility assay using an FPLC Superose 6 gel filtration column (Pharmacia Biotech, Uppsala, Sweden). Eluate was collected in one ml fractions. The void volume of this column is 8 ml. Previously, it was determined that wild type L1 VLPs predominantly elute in fraction 9 of the column, L1 capsomeres elute in fraction 15, and L1 monomers elute in fractions 19–21 (Okun, M. M. et al., submitted for publication). Column fractions were assayed for the presence of L1 by Western blot.

Example 2 describes the methods used to confirm that a chimeric L1-CCR5 protein self-assembled into capsomeric structures. Interestingly, the L1-CCR5 particles described below were shown by electron microscopy to be somewhat smaller than VLPs formed of wild type L1 proteins.

EXAMPLE 2

Preparation of Chimeric Capsomeric Structures

The three above-described L1-CCR5 chimeras were isolated by FPLC SUPEROSE 6 gel filtration column chromatography (Pharmacia Biotech, Uppsala, Sweden). Column fractions of 1 ml each were assayed for the presence of L1 by Western blotting using a 10% polyacrylamide gel under denaturing conditions. Control procedures indicated that wild type L1 VLPs predominantly eluted in the column fraction 9, that L1 capsomeres eluted in fraction 15, and that L1 monomers eluted in fractions 19–21. L1-CCR5 protein from preparations of chimeras 2 and 3 was detected predominantly in fraction 15. These results suggested that L1-CCR5 chimera 2 and L1-CCR5 chimera 3 proteins failed to assemble into higher order structures. Based on these results, we selected the L1-CCR5 chimera 1 for subsequent procedures. Purified particles were examined using electron microscopy by first adsorbing the particles to carbon-coated grids, staining with 1% uranyl acetate and then examining the grids using a Philips electron microscope model EM 400RT at 36,000×magnification.

Results of these procedures indicated that the L1-CCR5 chimera 1 protein eluted in a column fraction known to contain assembled particulate structures. Examination of chimera 1 particles by electron microscopy revealed particles having diameters of approximately 28 nm while wild type L1 VLPs had diameters of approximately 55 nm. The 28 nm diameter suggests that the particles were composed of 12 capsomeres while the larger diameter structures formed of wild type L1 proteins were composed of 72 capsomeres. Morphologically, the L1-CCR5 chimera 1 particles resembled polyomavirus 12 ICOSA shells (T=1 particles) which are composed of a regular array of 12 pentameric capsomeres of the polyomavirus major coat protein VP1 and can be generated upon in vitro reassembly of VP1 capsomeres at high ionic strength (Salunke, et al., *Biophys. J.*, 56:887 (1989)). Small particles of a size similar to the L1-CCR5 particles were found as minor components of wild type BPV-1 L1 VLP preparations. Although the L1-CCR5 particles were smaller than wild type VLPs, they possessed at least some characteristics of wild type VLPs that wild type capsomeres lack. In particular, L1-CCR5 particles hemagglutinated mouse red blood cells and displayed ELISA reactivity to a BPV-1 neutralizing monoclonal antibody (#9), which specifically bound to particles but not capsomeres (Roden, et al., *J. Virol.*, 68:7570 (1994)).

The following Example illustrates how peptide sequences displayed as ordered arrays on capsomeric structures can stimulate humoral immune responses, even against central antigens. As indicated below, mice administered with L1-CCR5 particles responded by producing mCCR5 specific antibodies. Significantly, the results indicated that the immunization overcame B cell tolerance to the peptide without affecting tolerance to endogenous cellular CCR5. The anti-self antibodies induced by the immunogenic particles bound native mCCR5, blocked binding of a CCR5 ligand and inhibited HIV-1 infection through a chimeric CCR5 protein that contained the mCCR5 peptide.

Example 3 describes the methods used to demonstrate that chimeric L1-CCR5 particles could be used as immunogens to induce anti-CCR5 antibodies.

EXAMPLE 3

Stimulation of a Tolerance Breaking Immune Response

To prepare antisera, C57B1/6 mice were administered in an immunization protocol with either: L1-CCR5 particles, wild type BPV-1 L1 VLPs, or a synthetic CCR5 peptide representing the first extracellular loop of mCCR5 that was coupled to keyhole limpet hemocyanin (KLH) using an IMJECT activated immunogen conjugation kit (Pierce, Rockford, Ill.). In some cases, mice were administered with L1-CCR5 particles that had been denatured by boiling for 2 minutes in the presence of 1% SDS. Mice were innoculated intradermally with 10 µg of antigen three times at two-week intervals. In most cases, serum samples were collected two weeks after the final boost. When adjuvant was used, the antigen was prepared in Freund's complete adjuvant for the initial injection, and in Freund's incomplete adjuvant for subsequent injections. Serum samples were tested for reactivity against the CCR5 peptide and against wild type VLPs using a quantitative ELISA protocol to detect IgG antibody against BPV-1 VLPs. The ELISA was performed using the procedure described by Kimbauer et al., in *J. Natl. Cancer Inst.*, 86:494 (1994). A synthetic peptide representing the first extracellular loop of mCCR5 was prepared and coupled to bovine serum albumin (BSA) as a carrier protein. Anti-CCR5 specific IgG was detected by binding 300 ng BSA-coupled CCR5 peptide in 50 µl phosphate buffered saline (PBS) to each well of a 96-well IMMULON II microtiter plate (Dynatech; Chantilly, Va.) for 2 hours at 37° C. After washing three times with PBS, the wells were blocked for 2 hours with 50 µl of PBS containing 0.5% nonfat dry milk plus 1% newborn calf serum at room temperature. After blocking, the wells were again washed three times with PBS thereafter. Mouse serum was serially diluted in PBS plus 0.5% nonfat dry milk. Diluted serum samples (50 µl) were applied to the wells after removing the final PBS wash. Plates were incubated at room temperature for 2.5 hours with gentle rocking. After five washes, 50 µl of horseradish peroxidase conjugated goat anti-mouse IgG (Boehringer Mannheim; Indianapolis, Ind.) diluted 1:10,000 in 0.5% milk-PBS was added to the wells. Plates were incubated at room temperature for 1 hour with gentle rocking and then washed three times. The ABTS peroxidase substrate (50 µl) (Boehringer Mannheim) was added to the plate, incubated for 45 minutes at room temperature, and optical densities (ODs) read at 405 nm using a THERMO MAX microplate reader. $OD_{405}$ values greater than twice background (usually greater than 0.1) were considered positive.

The results presented in FIG. 1A indicated that serum samples from mice administered with L1-CCR5 particles had high anti-CCR5 ELISA titers. In contrast, control mice administered with wild type VLPs had no ELISA reactivity, as expected. Anti-CCR5 titers ranged from $3 \times 10^3$ to $3 \times 10^4$ in the three animals that had been administered with the immunogen in combination with Freund's adjuvant, and measured $3 \times 10^3$ in the two animals that had received the immunogen without adjuvant. Mice administered with denatured L1-CCR5 particles in combination with adjuvant showed no evidence for mCCR5 peptide-specific antibodies. The lack of reactivity of the denatured L1-CCR5 particles was limited to the CCR5 peptide since, as indicated by the results presented in FIG. 1B, the denatured material elicited high titers of anti-L1 antibodies. These findings clearly demonstrated that adult mammals retained the ability to produce antibodies specific for central self antigens.

While the foregoing results indicated that the L1-CCR5 particles elicited antibodies specific for the CCR5 peptide, further testing was conducted to verify that the antibodies also recognized cell-associated mCCR5 protein when displayed in its native conformation. This was accomplished using flow cytometric analysis (FACS) to show that the anti-CCR5 antibodies bound mCCR5 expressed on the cell surface.

Example 4 describes the methods used to demonstrate that antibodies raised against the L1-CCR5 particles bound authentic mCCR5 receptor protein expressed on cell surfaces.

EXAMPLE 4

Binding of Native Antigen by Autoantibodies Stimulated in Response to a Self Antigen Incorporated into a Capsomeric Structure Total IgG from pooled mouse sera was affinity purified over a Protein G column (Pierce) using procedures that will be familiar to those having ordinary skill in the art. Column fractions containing IgG were pooled and then concentrated using a CENTRICON-30 spin column (Amicon; Beverly, Mass.). Antibody binding assays were conducted using transfected human cells that expressed a recombinant mouse CCR5 receptor. The binding of antibodies raised against L1-CCR5 particles could not be tested easily using primary cultures of mouse cells because these cells expressed high levels of Fcγ receptors and yielded high background levels of binding due to interactions with non-specific mouse IgG. Accordingly, for flow cytometry analysis a mouse CCR5 expression vector was transiently expressed in HeLa-MAGI cells by transfection using a LIPOFECTAMINE PLUS transfection kit (Gibco BRL; Gaithersberg, Md.). pcDNA3 derived plasmids containing mCCR5 cloned from B6 mice and a human-mouse CCR5 chimera containing the first extracellular loop of mCCR5 in a background of human CCR5 were prepared as described by Kulunann et al., in $J.$ $Virol.,$ 71:8642 (1997). Monolayers were detached by gentle scraping in the presence of 5 mM EDTA at 48 hours post-transfection. Cells were washed three times in staining buffer (PBS plus 0.5% BSA). Approximately $10^5$ cells were resuspended in 25 μl staining buffer plus 1 μg of mouse IgG and then incubated 45 minutes at 4° C. Cells were washed three times with staining buffer, resuspended in 25 μl of staining buffer plus 250 ng fluorescein (FITC)-labelled goat anti-mouse IgG (Jackson Immunoresearch; West Grove, Pa.), and incubated for 30 minutes at 4° C. Cells were washed three times with staining buffer and finally resuspended in 0.5 ml staining buffer in preparation for FACS analysis. As a control, cells were stained with 500 ng FITC-labelled mouse anti-human CCR5 monoclonal antibody (mAB182) (R & D Systems; Minneapolis, Minn.) according to the manufacturers specifications. FACS analysis was performed using a FACSCALIBUR and CELLQUEST software (Becton Dickinson; San Jose, Calif.). Specific binding was measured relative to staining of control cells transfected with the pcDNA3 vector.

Results from these procedures indicated that autoantibodies stimulated in response to administration of L1-CCR5 capsomeric particles specifically bound recombinant mCCR5 receptors expressed on the surface of transfected HeLa-MAGI cells. FIG. 2A shows that IgG from mice immunized with L1-CCR5 bound specifically with high affinity to transfected cells that expressed the mCCR5 receptor but not to cells transfected with vector alone. Cells expressing mCCR5 did not substantially bind antibodies that were stimulated in response to immunization with virus-like particles formed by wild type L1 (FIG. 2B) or a monoclonal antibody (mAB182) specific for the second extracellular loop of human CCR5 (FIG. 2C), as expected. As a control for antibody specificity, mice were administered with mCCR5 peptide that had been coupled to keyhole limpet hemocyanin (KLH). While these mice responded by producing anti-CCR5 peptide antibodies having ELISA titers of $10^5$ against a BSA-coupled, purified IgG failed to bind cells expressing mCCR5 (FIG. 2D). In aggregate, these results indicated that antibodies raised in response to immunization with L1-CCR5 capsomeric particles functioned as true autoantibodies because they specifically bound cell surface-expressed native mCCR5, in contrast to the antibodies raised against the KLH-CCR5 peptide.

The ability of antibodies raised against L1-CCR5 particles to bind native mCCR5 was further examined by testing for competition with the $^{125}$I-labelled human RANTES chemokine ligand for binding to transfected HeLa-MAGI cells expressing mCCR5. The mouse chemokines MIP-1α, MIP-1β and RANTES are ligands for mCCR5. In addition, the human homologs of MIP-1β and RANTES are able to bind mCCR5 (Meyer et al., $J.$ $Biol.$ $Chem.,$ 271:14445 (1996); Nibbs et al., $J.$ $Biol.$ $Chem.,$ 272:12495 (1997)). As described in the following Example, cells were incubated with 0.5 nM iodinated RANTES in the absence or presence of dilutions of mouse sera three days after transfection with a mCCR5 expression construct.

Example 5 describes the methods used to demonstrate that autoantibodies raised against the CCR5 receptor inhibited ligand binding to the receptor.

EXAMPLE 5

Autoantibodies Specific for a Receptor Inhibit Ligand Binding

HeLa-MAGI cells were transiently transfected with the mCCR5 expression plasmid using a $CaPO_4$ transfection kit that was purchased from Stratagene Cloning Systems (La Jolla, Calif.). At two days post-transfection $10^5$ cells were transferred into individual wells of a 24-well tissue culture plate. The following day cells were washed twice in cold PBS and then resuspended in 150 μl cold binding buffer (25 mM HEPES (pH 7.2), 5 mM $MgCl_2$,1 mM $CaCl_2$,0.5% (wt/vol) BSA). *Cells were incubated for* 4 hours at 4° C. with 0.5 nM $^{125}$I-labelled human RANTES (Amersham; Arlington Heights, Ill.) in the absence or presence of various dilutions of mouse sera. To remove small molecules, mouse sera was buffer exchanged into binding buffer using MICRO BIO-SPIN CHROMATOGRAPHY-6 columns (Bio-Rad, Hercules, Calif.) prior to conducting the binding assays. As a control, some binding assays were performed in the presence of 50 nM or 500 nM non-iodinated human RANTES (R & D Systems). Reactions were stopped by washing the wells four times with cold binding buffer plus 0.5 M NaCl. Cells were lysed by adding 0.5 ml 1% SDS, and the lysates transferred to counting vials. Bound radioactivity was counted for 1 minute in a Beckman Gamma 5500B counter.

Results from these procedures confirmed that autoantibodies raised against the L1-CCR5 particles specifically bound cell surface expressed CCR5 and inhibited ligand binding to the receptor. More particularly, the graphic results shown in FIG. 4 indicated that a 1:30 dilution of L1-CCR5 sera displaced approximately 66% of the iodinated human RANTES (similar to the displacement observed using a 100-fold excess of cold RANTES), compared with 37% displacement with a 1:30 dilution of wild type L1 VLP sera. The 1:75 and 1:150 dilutions of L1-CCR5 sera displaced 25% and 17% of the iodinated RANTES, respectively, whereas no significant displacement was observed using control sera at these dilutions. Maximally bound iodinated RANTES was determined by assaying for binding in the absence of sera, and corresponded to approximately 2550 cpm indicated by the dashed horizontal line in FIG. 3. Non-specific binding of iodinated RANTES (approximately 1300 cpm) was determined by assaying for binding in a 1000-fold excess (500 nM) of cold (non-iodinated) human RANTES. Data shown in FIG. 4 represents the average of duplicate wells from one experiment. Previous studies have suggested MIP-1α, MIP-1β and RANTES bind to the second extracellular loop of human (h) CCR5, since their binding was blocked by monoclonal antibody to this portion of the molecule but not by an antibody specific for the amino terminus of hCCR5 (Wu et al., *J. Exp. Med.,* 186:1373 (1997)). The findings presented herein indicated that antibodies having binding specificity for the first extracellular loop of mCCR5, which is located between these two sites, advantageously inhibited RANTES binding and further provided a way to stimulate formation of these autoantibodies in vivo.

To further investigate the utility of the above-described autoantibodies, we investigated whether the inhibition of ligand binding observed in the foregoing Example correlated with inhibition of viral infection of target cells. Monoclonal antibody studies have implicated the second extracellular loop and the amino terminal region of hCCR5, and studies of chimeric receptors have indicated that the first and third extracellular loops of CCR5 also contribute to receptor interaction with HIV-1 (Wu et al., *J. Exp. Med.,* 186:1373 (1997); Rucker et al., *Cell,* 87:437 (1996); Atchison et al., *Science,* 274:1924 (1996); Alkhatib et al., *J. Biol. Chem.,* 272:19771 (1997); Picard et al., *J. Virol.,* 71:5003 (1997); Ross et al., *J. Virol.,* 72:1918 (1998)). Although mCCR5 does not function as an HIV-1 co-receptor, a human-mouse chimeric receptor (HMHH), which contains the first extracellular loop of mCCR5 (the B6 mouse sequence) in a background of hCCR5, has co-receptor activity when expressed in human cell lines (Kuhmann et al., *J. Virol.,* 71:8642 (1997)). Accordingly, this chimeric receptor was used in the following Example to test whether anti-L1-CCR5 sera could block M-tropic HIV-1 infection.

The results presented in the following Example have strong bearing on the inhibition of HIV infection because even partial reduction in CCR5 expression can have clinically significant effects. This is true because HIV-1 infected individuals who are heterozygous for an inactive CCR5 allele exhibit delayed progression to AIDS (Liu et al., *Cell,* 86:367 (1996); Samson et al., *Nature,* 382:722 (1996); Winkler et al., *Science,* 279:389 (1998)).

Example 6 describes the methods used to demonstrate that autoantibodies raised in response to L1-CCR5 particles inhibited infection of target cells by M-tropic HIV-1. Since a chimeric mouse-human CCR5 receptor was used in these procedures, the initial step involved confirming that the above-described anti-CCR5 autoantibodies recognized the chimeric receptor.

EXAMPLE 6

Anti-Receptor Autoantibodies Inhibit HIV Infection of Target Cells

To confirm that IgG purified from L1-CCR5 sera bound the human-mouse chimeric receptor, FACS analysis was performed on HeLa-MAGI cells transiently transfected with the HMHH expression construct described by Kuhmann et al., in *J. Virol.,* 71:8642 (1997). The expression construct was transfected into recipient cells 2 days prior to staining with either L1-CCR5 IgG, wild type L1 VLP IgG or a positive control anti-human CCR5 monoclonal antibody. The results presented in FIGS. 2E–2G indicated that positive binding was obtained using serum IgG from mice administered with L1-CCR5 particles as well as with a positive control monoclonal antibody specific for the second extracellular loop of human CCR5. However, IgG from mice administered with wild type L1 VLP did not bind HMHH, as expected.

Based on the foregoing results, sera from L1-CCR5 mice were tested for the ability to inhibit infection of the M-tropic BaL strain of HIV-1, using a single replication cycle assay and the HeLa-MAGI indicator cell line. HeLa-MAGI cells, described by Kimpton et al., in *J. Virol.,* 66:2232 (1992), were transiently transfected with the chimeric human-mouse CCR5 expression vector using a commercially obtained $CaPO_4$ transfection kit (Stratagene Cloning Systems). Two days after transfection, and the day prior to infection, the indicator cells were seeded to 24-well plates at $6.5\times10^4$ cells per well in complete DMEM. Some infections were performed in the presence of pooled mouse sera which had been buffer-exchanged into PBS using MICRO BIO-SPIN CHROMATOGRAPHY-6 columns (Bio-Rad). Prior to infection, cells were incubated in a total volume of 140 μl in complete DMEM with 10 μg/ml DEAE-dextran plus dilutions of sera for 30 minutes at 4° C. After incubation, virus was added to each well to give a total volume of 150 μl. Cells were incubated for 2 hours at 37° C., then 1 ml of complete DMEM was added to each well. At 3 days post-infection cells were stained with X-gal and an infectious dose determined by counting the number of blue nuclei in infected wells. Inhibition of viral entry was scored by comparing the average number of blue nuclei in the presence of sera with average number of infectious centers in the absence of sera. Typically, enough infectious virions to lead to 50–75 infectious blue centers in control (no sera) wells were used in each infection. All assays were performed in duplicate. Over passage, the efficiency of infection of transfected HeLa-MAGI cells markedly decreased, presumably because of reduced CD4 expression. Therefore, all infections were performed on recently thawed HeLa-MAGI cells.

Results of these procedures, presented graphically in FIG. 4, showed that serum antibodies raised against the self CCR5 antigen, and that were shown to recognize native antigen and that inhibited ligand-receptor interactions, also inhibited viral infection of target cells. Indicator cells that were transiently transfected with the HMHH expression construct and contacted with HIV-1 BaL in the presence of L1-CCRS sera dilutions of 1:15, 1:30, and 1:75 exhibited 65%, 50%, and 45% neutralization of infectivity. At the same dilutions, control sera from wild type L1 VLP mice exhibited some non-specific neutralization, but only at a level of 25% at the 1:15 dilution and 15% at 1:30 and 1:75. Indicator cells infected with HIV-1 BaL in the presence of 50 μg/ml of a monoclonal antibody specific for human CCR5 (mAB182) that was used as a positive control exhibited approximately 50% neutralization. Thus, the anti-CCR5 autoantibodies produced in accordance with the procedure set forth above effectively inhibited infection of susceptible cells by HIV-1.

We have shown how to break B cell tolerance to a self antigen by presenting it in a context that mimics the ordered surface antigens of an infectious virus. To do this, we substituted a dominant virus-neutralizing epitope on the surface of papillomavirus L1 VLPs with a peptide sequence from a self protein. More specifically, we engineered into a putative neutralizing epitope in the L1 of bovine papillomavirus type 1 (BPV-1) (Ludmerer et al., *J. Virol.,* 70:4791 (1996)) a peptide sequence 16 amino acids in length which corresponded to the first external loop of the mouse chemokine receptor CCR5. This chimeric L1 assembled into particles having ordered arrays of capsomeres that could be used as immunogens for stimulating humoral immune responses against the chimeric L1-CCR5 protein.

Mice immunized with VLPs composed of chimeric L1-CCR5 protein subunits were maintained to determine the long term effects of the immunization, including any pathological consequences of autoantibody production. At six months post immunuization, the immunized mice weighed the same as control animals and appeared outwardly healthy. An autopsy of the mouse with the highest anti-CCR5 titers did not reveal any indications of autoimmune disease. The CCR5 antibody titers in the vaccinated mice were initially stable but then declined slowly, in parallel with the responses to L1. These results suggest that the cellular CCR5 neither activates nor tolerizes the chimeric VLP induced B cell response to the CCR5 peptide.

The following Example describes how autoantibodies directed to a central self antigen can be stimulated in a mammal other than a mouse. In the exemplary case illustrated below a composition and method for inducing production of anti-macaque CCR5 antibodies is described.

EXAMPLE 7

Stimulation of an Autoimmune Response in Macaques

A recombinant expression construct encoding a chimeric L1-CCR5 protein which includes a portion of the macaque CCR5 polypeptide sequence was first prepared essentially according to the procedure set forth under Example 1. The resulting expression construct was introduced into recipient Sf9 cells where protein encoded by the recombinant vector was produced. Capsomeric structures representing self-assembled aggregates of the chimeric L1-CCR5 protein produced in the recipient cells were purified by sucrose gradient and CsCl gradient centrifugation. In a parallel procedure, wild type VLPs composed of wild type L1 protein also were prepared and purified for use as a control immunogen. The control immunogen does not contain the macaque CCR5 polypeptide sequence that is present in the L1-CCR5 chimera. Purified wild type VLPs or chimeric L1-CCR5, combined with adjuvant capsomeric structures, give control and test immunogenic compositions, respectively. These compositions are separately injected intradermally into macaques according to a standard immunization protocol such as that described under Example 3. In one instance the animals are administered with the immunogenic compositions three times at two week intervals. Serum samples taken from the two animals periodically from a time before the initial immunization indicated no evidence for CCR5-binding antibodies before immunization. Serum samples from the control animal show no evidence for CCR5-binding antibodies even several weeks after the final administration of the wild type L1 VLP immunogenic composition. In contrast, serum samples from the animal administered with capsomeric structures that included the L1-CCR5 chimera contain significant levels of anti-CCR5 antibodies. (FIG. 5). These results confirmed that the L1-CCR5 capsomeric structures have the desired immunogenicity and that the effect is antigen-specific.

We have previously shown that addition of other papillomavirus polypeptides to the VLPs, as fusions of the L2 minor capsid protein, can induce a strong cell mediated immune response against these viral peptides and the production of specific antibodies against the inserted peptide (Greenstone et al., *Proc Natl Acad Sci USA*, 95:1800 (1998); H. L. Greenstone Ph.D. Thesis (1998), The Johns Hopkins University, Baltimore, Md.). Both induction of high titer antibody responses and MHC I restricted CTL responses can be induced by low dose inoculation of VLPs in the absence of adjuvant. In view of the findings presented above, the capacity of VLPs to induce potent immune responses against viral epitopes is probably related to their ability to interact with cell surfaces and to present epitopes as an ordered array of repetitive structure.

We have had success generating L2 chimeras of viral proteins. Significantly, all of the fusions were compatible with co-assembly into full-sized L1 VLPs that could be efficiently recovered as particles (Greenstone et al., *Proc Natl Acad Sci USA*, 95:1800 (1998)). Large inserts, even representing 42 kDa full-length proteins, in the L2 protein were compatible with VLP assembly. The ability of the L2 to accept inserts of this size is attributed to the fact that L2 does not contribute to the structural integrity of the VLP and so can tolerate substantial modification without compromising particle self-assembly. While it is likely that L2 has an ordered structure in the VLPs, its spacing probably is not as close as the spacing of L1. Although the location of L2 in the papillomavirus capsid has not been definitively determined, we have experimental evidence showing that L2 is located at the twelve vertices of the icosahedral capsid. This would place L2 and any peptide inserted therein at a repeat distance of approximately 300 angstroms.

Since the papillomavirus L2 protein can accommodate large inserts of extraneous polypeptide sequence and still incorporate into virus-like particles, L1/L2 chimeras having full-length self proteins inserted at the site of L2 can be prepared and used as immunogens. In a preferred embodiment the target polypeptide is fused to the first 110 amino acids of the BPV L2 protein. This presents the insert sequence on the capsid exterior when assembled into L1 VLPs. Indeed, this approach can be used to prepare chimeric VLPs that can be used as immunogens for stimulating production of autoantibodies against TNF-α.

The following two Examples describe how to make mouse TNF-α VLPs both as L2 chimeras and as streptavidin fusions. Based upon the known atomic structure of the protein (Eck et al., *J. Biol. Chem.*, 264:17595 (1989)), L1 chimeras also can be prepared by inserting TNF-α peptides that include epitopes to which functionally neutralizing antibodies bind. Serum from TNF-α-VLP vaccinated mice can be tested for reactivity against mouse TNF-α in an ELISA assay and for inhibition of TNF-α induced cytolysis of L929 cells in vitro (Takasaki et al., *Nature Biotech*, 15:1266 (1997)). The VLPs displaying the TNF-α polypeptide sequence can also be used to vaccinate DBA/1 mice having collagen type II RA. The effect of this treatment on the course of disease can be monitored using standard paw swelling and histological analyses (Thorbecke et al., *Proc. Natl. Acad. Sci. USA*, 89:7375 (1992)).

Example 8 describes a method that can be used to prepare chimeric L1/L2 particles for use as immunogens.

EXAMPLE 8

Chimeric L1/L2 Particles to Stimulate Production of Autoantibodies

Using standard techniques that will be familiar to those having ordinary skill in the art of molecular cloning, genetic constructs encoding L2-mouse TNF-α polypeptide chimeras are prepared and expressed within transfected cells as chimeric proteins. The chimeric proteins are then co-assembled into L1 virus-like particles to result in chimeric L1/L2 VLPs. The L1/L2 VLPs are purified, combined with an adjuvant and administered to test animals in an immunization protocol. As controls, the L2-TNF-α chimeric protein and soluble TNF-α are injected alone. Serum samples from the mice administered with the chimeric L1/L2 VLP preparation contain anti-TNF-α antibodies that are detectable in an ELISA assay. In contrast, serum samples from control animals do not contain anti-TNF-α antibodies. This result indicates that chimeric L1 /L2 particles that include chimeric L2 proteins are useful for stimulating production of autoantibodies.

Example 9 describes a method for making and using immunogenic virus-like particles wherein a self polypeptide sequence is joined to the proteins which make up the particle through a biotin linkage. In this instance, pre-formed VLPs are biotinylated and then contacted with an streptavidin-linked self peptide. This manipulation is possible because wild type L1 VLPs are quite stable once they are formed.

EXAMPLE 9

Virus-Like Particles Incorporating Self Polypeptides Through a Biotin Linkage Purified wild type L1 VLPs were biotinylated using sulfo-NHS-Biotin reagents according to the manufacturer's instructions (Pierce). Biotinylated VLPs were purified from free biotin by separation on a 24%–54% linear sucrose gradient. Preliminary experiments demonstrated that L1 VLPs were heavily biotinylated. This observation indicated that there was at least one exposed lysine for biotin attachment on each L1. A mouse TNF-α polypeptide was conjugated to the VLPs as a streptavidin fusion protein. Streptavidin was generally useful for efficiently attaching any polypeptide of choice to the biotinylated VLPs. The polypeptide sequence from the mouse TNF-α protein had the sequence: Ser-Ser-Gln-Asn-Ser-Ser-Asp-Lys-Pro-Val-Ala-His-Val-Val-Ala-Asn-His-Gln-Val-Glu (SEQ ID NO:2). This sequence was cloned as a C-terminal fusion into the streptavidin expression vector pTSA-18 F. (Sano, T. and Cantor, C. R., *Biochem. Biophy. Res. Commun.,* 176:571–577 (1991)). Expression was performed in BL21 (DE3)(pLysS) bacteria incubated for 3–6 hours after induction with 0.4 mM IPTG. Purification of the protein from inclusion bodies was performed as described by Sano and Cantor. (Sano, T. and Cantor, C. R., *Proc. Natl. Acad. Sci USA,* 87:142–146 (1990)). The streptavidin fusion protein was reacted with biotinylated VLPs at a 3:1 weight:weight ratio for 1 hour at room temperature. Particles conjugated to the streptavidin fusion were purified by centrifugation on a 24%–54% linear sucrose gradient. Preparations of 5 μg VLPs with or without attached streptavidin-linked self polypeptide were injected into test and control mice, respectively, three times at two-week intervals. Two weeks after the final injection, serum samples taken from the animal administered with the composition that included the self polypeptide showed evidence for anti-self polypeptide antibodies. In contrast, corresponding antibodies were not detected in serum samples from the control animals.

It is well established that mouse monoclonal antibodies are useful as therapeutic agents and as reagents for a variety of basic and applied studies. However, since most monoclonal antibodies are of mouse or rat origin, the currently available set of antibodies is deficient in those that specifically recognize mouse or rat epitopes displayed on the surface of central antigens in their native conformation. This deficiency is limiting for human studies because rodents are models for studying mammalian biology and highly conserved amino acid sequences of protein typically have important functions that are conserved through evolution. Accordingly, using the methods disclosed herein it will be possible to stimulate B cell responses against self antigens in their native conformation. Thereafter it will be possible to prepare and screen for hybridomas producing monoclonal antibodies having the desired binding specificity. Specifically, the TNF-α VLP that is most effective in generating polyclonal antibodies against TNF-α will used in an attempt to generate monoclonal antibodies that specifically recognize and functionally inactivate mouse TNF-α. The standard spleen cells/myeloma fusion method will be used to generate the monoclonal antibody producing cells (Galfre et al., *Nature,* 266:550 (1977)).

Example 10 briefly describes a method that can be used to produce mouse monoclonal antibodies against TNF-α.

EXAMPLE 10

Production of Monoclonal Antibodies

Mice are first immunized with virus-like particles displaying on their surface a mouse TNF-α polypeptide prepared according to the above-described methods. It is established using an ELISA assay that the serum from the mice contains antibodies specific for native TNF-α. The mice are sacrificed, and harvested spleen cells are fused with non-secreting myeloma cells to produce a collection of hybridomas. The hybridomas are screened by methods that will be familiar to those having ordinary skill in the art to identify those secreting antibodies having binding specificity for native TNF-α. Useful quantities of the anti-TNF-α antibodies are then purified.

EXAMPLE 11

Increasing Antibody Response to Subdominant Virus Neutralizing Epitopes

Vaccination with papillomavirus L1 and L1/L2 VLPs can generate high titer (greater than 100,000) but only type specific neutralizing antisera (Kimbauer, R. et al., *PNAS,* 89:12180–4 (1992); Roden, R. et al., *J. Virol.,* 70:5875–83 (1996)). In contrast, L2 alone or fragments thereof elicit only low titers of neutralizing antisera (1000 or less), but they can be cross-neutralizing among papillomavirus types (Roden, R. et al., *J. Viro.,* 68:75704 (1994); Kawana, K. et al., *J. Virol.,* 73:6188–90 (1999); Roden, R. et al., *Abstract Book* 17th *International Papillomavirus Conference,* p. 61 (1999)). To increase the titers of cross-neutralizing L2 antibodies, L2 peptides are displayed in a closely spaced array on the surface of VLPs. For example, a peptide including amino acids 108–120 of HPV 16 L2 is genetically fused to the C terminus of streptavidin and the fusion protein is produced as described in Example 9. The streptavidin-L2 fusion protein is reacted with biotinylated VLPs and the conjugated VLPs purified as outlined in Example 9. Antisera from streptavidin-L2 conjugated VLP vaccinated mammals are tested for antibodies that cross-neutralize papillomavirus pseudo virions, using the previously described in vitro neutralizing assays (Roden, R. et al., *J. Virol.,* 68:7570–4 (1994); Roden, R. et al., *Abstract Book,* 17th *International Papillomavirus Conference,* p. 61 (1999)). High titers of cross-neutralizing antibodies are detected.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed:

1. A composition comprising:
   a capsomeric structure having a symmetrical assembly of capsid proteins; and
   at least one B cell epitope of a tolerogen joined to the capsomeric structure so as to form a tolerogen presenting capsomeric structure, wherein the tolerogen presenting capsomeric structure displays the tolerogen on the surface thereof in an ordered, repetitive array having a spacing of about 100 angstroms.

2. The composition of claim 1, wherein the capsid protein is a capsid protein from a virus selected from the group consisting of papillomavirinae, polyomavirinae, and parvoviridae.

3. The composition of claim 1, wherein the capsid protein is a papillomavirus L1 protein.

4. The composition of claim 1, wherein the capsomeric structure is icosahedral.

5. The composition of any of claims 1–4, wherein the tolerogen is joined to the capsomeric structure by a linker.

6. The composition of claim 1, wherein the linker comprises biotin.

7. The composition of any of any claims 1–4, wherein the tolerogen is selected from the group consisting of a peptide, carbohydrate and lipid.

8. The composition of any of claims 1–4, wherein the tolerogen is a self antigen.

* * * * *

UNITED STATES PATENT AND TRADEMARK OFFICE
CERTIFICATE OF CORRECTION

PATENT NO. : 6,719,978 B2
DATED : April 13, 2004
INVENTOR(S) : Schiller et al.

It is certified that error appears in the above-identified patent and that said Letters Patent is hereby corrected as shown below:

Column 38,
Line 36, delete the word "any."

Signed and Sealed this

Twenty-eighth Day of June, 2005

JON W. DUDAS
*Director of the United States Patent and Trademark Office*

UNITED STATES PATENT AND TRADEMARK OFFICE
CERTIFICATE OF CORRECTION

PATENT NO.      : 6,719,978 B2
DATED           : April 13, 2004
INVENTOR(S)     : Schiller et al.

It is certified that error appears in the above-identified patent and that said Letters Patent is hereby corrected as shown below:

Column 38,
Line 36, delete "The composition of any of any claims 1-4" and insert -- The composition of any of claims 1-4 --.

Signed and Sealed this

Tenth Day of January, 2006

JON W. DUDAS
*Director of the United States Patent and Trademark Office*